United States Patent
Merriman et al.

(10) Patent No.: US 10,036,064 B2
(45) Date of Patent: Jul. 31, 2018

(54) BIOMOLECULAR SENSORS AND METHODS

(71) Applicant: Roswell Biotechnologies, Inc., San Diego, CA (US)

(72) Inventors: Barry L. Merriman, San Diego, CA (US); Paul W. Mola, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

(21) Appl. No.: 15/336,557

(22) Filed: Oct. 27, 2016

(65) Prior Publication Data

US 2017/0044605 A1  Feb. 16, 2017

Related U.S. Application Data

(63) Continuation of application No. PCT/US2016/039446, filed on Jun. 24, 2016.
(Continued)

(51) Int. Cl.
 *C12Q 1/6869* (2018.01)
 *G01N 27/327* (2006.01)
(Continued)

(52) U.S. Cl.
 CPC ........... *C12Q 1/6869* (2013.01); *G01N 27/26* (2013.01); *G01N 27/327* (2013.01); *G01N 27/3272* (2013.01); *G01N 27/3276* (2013.01); *G01N 27/3278* (2013.01); *G01N 27/4145* (2013.01); *B82Y 15/00* (2013.01); *B82Y 40/00* (2013.01)

(58) Field of Classification Search
 CPC ........... C12Q 1/001–1/003; C12Q 1/68; C12Q 1/6834; C12Q 1/6837; C12Q 1/6869; G01N 27/327–27/3278
 See application file for complete search history.

(56) References Cited

U.S. PATENT DOCUMENTS

| | | | |
|---|---|---|---|
| 5,082,627 | A | 1/1992 | Stanbro |
| 5,194,133 | A | 3/1993 | Clark et al. |

(Continued)

FOREIGN PATENT DOCUMENTS

| | | |
|---|---|---|
| KR | 20070059880 | 6/2007 |
| KR | 20110104245 | 9/2011 |

(Continued)

OTHER PUBLICATIONS

H. Nishida, et al. Self-Oriented Immobilization of DNA Polymerase Tagged by Titanium-Binding Peptide Motif, Langmuir, 31, pp. 732-740 (first published Dec. 17, 2014).*

(Continued)

*Primary Examiner* — Maris R Kessel
(74) *Attorney, Agent, or Firm* — Snell & Wilmer LLP

(57) ABSTRACT

Electronic sensors configured to detect single molecule targets and methods of using and manufacturing such electronic sensors are disclosed. A sensor may include a first electrode and a second electrode separated by a sensor gap. The first and second electrodes can be coupled by a sensor complex that can include a biopolymer bridge molecule and a probe. The probe can interact with a target molecule, and interaction of the probe and target molecule can produce a signal suitable to provide detection of the target molecule.

25 Claims, 18 Drawing Sheets

Related U.S. Application Data

(60) Provisional application No. 62/184,776, filed on Jun. 25, 2015.

(51) Int. Cl.
  *G01N 27/26* (2006.01)
  *G01N 27/414* (2006.01)
  *B82Y 15/00* (2011.01)
  *B82Y 40/00* (2011.01)

(56) References Cited

U.S. PATENT DOCUMENTS

| | | | |
|---|---|---|---|
| 5,366,140 A | 11/1994 | Koskenmaki et al. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,871,918 A | 2/1999 | Thorp et al. | |
| 5,982,018 A | 11/1999 | Wark | |
| 6,051,380 A | 4/2000 | Sosnowski et al. | |
| 6,094,335 A | 7/2000 | Early | |
| 6,110,354 A | 8/2000 | Saban | |
| 6,123,819 A | 9/2000 | Peeters | |
| 6,144,023 A | 11/2000 | Clerc | |
| 6,440,662 B1 | 8/2002 | Gerwen et al. | |
| 6,464,889 B1 | 10/2002 | Lee et al. | |
| 6,506,564 B1* | 1/2003 | Mirkin | B82Y 5/00 435/6.11 |
| 6,537,747 B1 | 3/2003 | Mills, Jr. et al. | |
| 6,670,131 B2 | 12/2003 | Hashimoto | |
| 6,716,620 B2 | 4/2004 | Bashir et al. | |
| 6,749,731 B2 | 6/2004 | Kobori | |
| 6,764,745 B1 | 7/2004 | Karasawa et al. | |
| 6,790,341 B1 | 9/2004 | Saban | |
| 6,861,224 B2 | 3/2005 | Fujita et al. | |
| 6,916,614 B1 | 7/2005 | Takenaka et al. | |
| 6,958,216 B2 | 10/2005 | Kelley | |
| 7,169,272 B2 | 1/2007 | Fritsch et al. | |
| 7,183,055 B2 | 2/2007 | Van Der Weide | |
| 7,189,435 B2 | 3/2007 | Tuominen et al. | |
| 7,202,480 B2 | 4/2007 | Yokoi et al. | |
| 7,276,206 B2 | 10/2007 | Augustine et al. | |
| 7,399,585 B2 | 7/2008 | Gau | |
| 7,470,533 B2 | 12/2008 | Xu et al. | |
| 7,507,320 B2 | 3/2009 | Hwang et al. | |
| 7,531,120 B2 | 5/2009 | Van Rijn et al. | |
| 7,579,823 B1 | 8/2009 | Ayliffe | |
| 7,691,433 B2 | 4/2010 | Kronholz et al. | |
| 7,943,394 B2 | 5/2011 | Flandre et al. | |
| 8,241,508 B2 | 8/2012 | D'Urso et al. | |
| 8,591,816 B2 | 11/2013 | Calatzis et al. | |
| 8,652,768 B1 | 2/2014 | Huber et al. | |
| 8,753,893 B2 | 6/2014 | Liu et al. | |
| 8,940,663 B2 | 1/2015 | Iqbal et al. | |
| 9,108,880 B2 | 8/2015 | Jin et al. | |
| 9,829,456 B1 | 11/2017 | Merriman et al. | |
| 9,956,743 B2 | 5/2018 | Jin et al. | |
| 2002/0137083 A1 | 9/2002 | Kobori et al. | |
| 2002/0138049 A1 | 9/2002 | Allen et al. | |
| 2002/0142150 A1 | 10/2002 | Baumann et al. | |
| 2002/0184939 A1 | 12/2002 | Yadav | |
| 2003/0025133 A1 | 2/2003 | Brousseau | |
| 2003/0186263 A1 | 10/2003 | Frey et al. | |
| 2004/0014106 A1 | 1/2004 | Patno et al. | |
| 2004/0023253 A1* | 2/2004 | Kunwar | C12Q 1/003 435/6.11 |
| 2004/0038090 A1 | 2/2004 | Faris | |
| 2004/0063100 A1 | 4/2004 | Wang | |
| 2004/0086929 A1 | 5/2004 | Weide et al. | |
| 2004/0096866 A1* | 5/2004 | Hofmann | C12Q 1/6825 435/6.11 |
| 2004/0248282 A1 | 12/2004 | Sobha | |
| 2005/0029227 A1 | 2/2005 | Chapman | |
| 2005/0067086 A1 | 3/2005 | Ito et al. | |
| 2005/0172199 A1 | 8/2005 | Miller et al. | |
| 2005/0181195 A1 | 8/2005 | Dubrow | |
| 2005/0247573 A1 | 11/2005 | Nakamura et al. | |
| 2005/0285275 A1 | 12/2005 | Son | |
| 2006/0003482 A1 | 1/2006 | Chinthakindi et al. | |
| 2006/0024504 A1 | 2/2006 | Nelson et al. | |
| 2006/0024508 A1 | 2/2006 | D'Urso et al. | |
| 2006/0029808 A1 | 2/2006 | Zhai et al. | |
| 2006/0128239 A1 | 5/2006 | Nun et al. | |
| 2006/0147983 A1 | 7/2006 | O'uchi | |
| 2007/0026193 A1 | 2/2007 | Luzinov et al. | |
| 2007/0148815 A1 | 6/2007 | Chao et al. | |
| 2007/0184247 A1 | 9/2007 | Simpson et al. | |
| 2007/0207487 A1 | 9/2007 | Emig et al. | |
| 2007/0231542 A1 | 10/2007 | Deng | |
| 2008/0199657 A1 | 8/2008 | Capron et al. | |
| 2008/0199659 A1 | 8/2008 | Zhao | |
| 2009/0011222 A1 | 1/2009 | Xiu et al. | |
| 2009/0017571 A1 | 1/2009 | Nuckolls | |
| 2009/0020428 A1 | 1/2009 | Levitan | |
| 2009/0152109 A1 | 6/2009 | Whitehead et al. | |
| 2009/0170716 A1 | 7/2009 | Su et al. | |
| 2009/0295372 A1 | 12/2009 | Krstic et al. | |
| 2009/0297913 A1 | 12/2009 | Zhang et al. | |
| 2009/0324308 A1 | 12/2009 | Law et al. | |
| 2010/0038342 A1 | 2/2010 | Lim et al. | |
| 2010/0044212 A1 | 2/2010 | Kim et al. | |
| 2010/0055397 A1 | 3/2010 | Kurihara et al. | |
| 2010/0132771 A1 | 6/2010 | Lu | |
| 2010/0149530 A1 | 6/2010 | Tomaru | |
| 2010/0184062 A1* | 7/2010 | Steinmuller-Nethl | C12Q 1/6825 435/6.19 |
| 2010/0188109 A1 | 7/2010 | Edel et al. | |
| 2010/0194409 A1 | 8/2010 | Gao et al. | |
| 2010/0206367 A1 | 8/2010 | Jeong et al. | |
| 2010/0285275 A1 | 11/2010 | Baca et al. | |
| 2010/0285601 A1 | 11/2010 | Kong et al. | |
| 2010/0288543 A1 | 11/2010 | Hung et al. | |
| 2010/0300899 A1 | 12/2010 | Levine et al. | |
| 2011/0076783 A1 | 3/2011 | Liu et al. | |
| 2011/0091787 A1 | 4/2011 | McGrath et al. | |
| 2011/0227558 A1 | 9/2011 | Mannion et al. | |
| 2011/0229667 A1 | 9/2011 | Jin et al. | |
| 2012/0060905 A1 | 3/2012 | Fogel et al. | |
| 2013/0049158 A1 | 2/2013 | Hong et al. | |
| 2013/0108956 A1 | 5/2013 | Lu et al. | |
| 2013/0162276 A1 | 6/2013 | Lee et al. | |
| 2013/0183492 A1 | 7/2013 | Lee et al. | |
| 2013/0214875 A1 | 8/2013 | Duncan et al. | |
| 2013/0239349 A1 | 9/2013 | Knights et al. | |
| 2013/0245416 A1 | 9/2013 | Yarmush et al. | |
| 2013/0273340 A1 | 10/2013 | Neretina et al. | |
| 2013/0281325 A1 | 10/2013 | Elibol et al. | |
| 2013/0331299 A1 | 12/2013 | Reda et al. | |
| 2014/0001055 A1* | 1/2014 | Elibol | G01N 27/3278 205/777.5 |
| 2014/0011013 A1 | 1/2014 | Jin | |
| 2014/0027775 A1 | 1/2014 | Quick et al. | |
| 2014/0048776 A1* | 2/2014 | Huang | H01L 51/0093 257/40 |
| 2014/0170567 A1 | 6/2014 | Sakamoto et al. | |
| 2014/0174927 A1 | 6/2014 | Bashir et al. | |
| 2014/0197459 A1 | 7/2014 | Kis et al. | |
| 2014/0218637 A1 | 8/2014 | Gao et al. | |
| 2014/0253827 A1 | 9/2014 | Gao et al. | |
| 2014/0367749 A1 | 12/2014 | Bai et al. | |
| 2015/0005188 A1 | 1/2015 | Levner et al. | |
| 2015/0049332 A1 | 2/2015 | Sun et al. | |
| 2015/0057182 A1 | 2/2015 | Merriman et al. | |
| 2015/0191709 A1 | 7/2015 | Heron et al. | |
| 2015/0263203 A1 | 9/2015 | Lewis et al. | |
| 2015/0293025 A1 | 10/2015 | Ninomiya et al. | |
| 2015/0294875 A1 | 10/2015 | Khondaker et al. | |
| 2016/0017416 A1 | 1/2016 | Boyanov et al. | |
| 2016/0155971 A1 | 6/2016 | Strachan et al. | |
| 2016/0187282 A1 | 6/2016 | Gardner et al. | |
| 2016/0284811 A1 | 9/2016 | Yu et al. | |
| 2017/0240962 A1 | 8/2017 | Merriman | |

(56) References Cited

U.S. PATENT DOCUMENTS

| | | |
|---|---|---|
| 2018/0031508 A1 | 2/2018 | Jin |
| 2018/0031509 A1 | 2/2018 | Jin |
| 2018/0045665 A1 | 2/2018 | Jin |

FOREIGN PATENT DOCUMENTS

| | | | |
|---|---|---|---|
| WO | 200249980 | 6/2002 | |
| WO | WO-2005108612 A2 * | 11/2005 | ............... B82Y 5/00 |
| WO | 2007128965 | 1/2007 | |
| WO | 2007054649 | 5/2007 | |
| WO | 2007102960 | 9/2007 | |
| WO | 2007126432 | 11/2007 | |
| WO | 2010022107 | 2/2010 | |
| WO | 2012087352 | 6/2012 | |
| WO | 2013096851 | 6/2013 | |
| WO | 2015167019 | 11/2015 | |
| WO | 2015176990 | 11/2015 | |
| WO | 2015188197 | 12/2015 | |
| WO | 2016016635 | 2/2016 | |
| WO | 2016210986 | 12/2016 | |
| WO | 2017061129 | 4/2017 | |
| WO | 2017123416 | 7/2017 | |
| WO | 2017132567 | 8/2017 | |
| WO | 2017132586 | 8/2017 | |
| WO | 2017139493 | 8/2017 | |
| WO | 2017147187 | 8/2017 | |
| WO | 2017184677 | 10/2017 | |

OTHER PUBLICATIONS

G. Liu et al, An Enzyme-Based E-DNA Sensor for Sequence-Specific Detection of Femtomolar DNA Targets, J. Am. Chem. Soc., 2008, 130 (21), pp. 6820-6825.*

USPTO; Notice of Allowance dated Jan. 3, 2018 in U.S. Appl. No. 13/996,477.

PCT; International Search Report and Written Opinion dated Jan. 27, 2017 in Application No. PCT/US2017/015465.

PCT; International Search Report and Written Opinion dated Jan. 27, 2017 in Application No. PCT/US2017/015437.

PCT; International Search Report and Written Opinion dated Nov. 22, 2017 in Application No. PCT/US2017/044023.

PCT; International Search Report and Written Opinion dated Dec. 26, 2017 in Application No. PCT/US2017/044965.

International Search Report and Written Opinion dated Sep. 27, 2016 in Application No. PCT/US2016/039446.

USPTO; Advisory Action dated Mar. 14, 2017 in U.S. Appl. No. 15/050,270.

USPTO; Final Office Action dated Dec. 30, 2016 in U.S. Appl. No. 15/050,270.

USPTO; Non-Final Office Action dated Sep. 29, 2017 in U.S. Appl. No. 15/050,270.

USPTO; Non-Final Office Action dated Oct. 19, 2016 in U.S. Appl. No. 15/220,307.

USPTO; Notice of Allowance dated Jul. 28, 2017 in U.S. Appl. No. 15/220,307.

USPTO; Requirement for Restriction dated Dec. 1, 2016 in U.S. Appl. No. 13/996,477.

USPTO; Non-Final Office Action dated May 5, 2017 in U.S. Appl. No. 13/996,477.

USPTO; Final Office Action dated Oct. 4, 2017 in U.S. Appl. No. 13/996,477.

PCT; International Search Report and Written Opinion dated Apr. 8, 2010 in Application No. PCT/US2009/054235.

PCT; International Search Report and Written Opinion dated Nov. 29, 2012 in Application No. PCT/US2011/001995.

PCT; International Search Report and Written Opinion dated May 25, 2017 in Application No. PCT/US2017/18950.

PCT; International Search Report and Written Opinion dated Jul. 26. 2017 in Application No. PCT/US2017/017231.

PCT; International Search Report and Written Opinion dated Apr. 18. 2017 in Application No. PCT/US2016/68922.

Fink et al. "Electrical conduction through DNA molecules", Nature, vol. 398, pp. 407-410 (Jan. 20, 1999).

Stenning, "The Investigation of Grain Boundary Development and Crystal Synthesis of Thin Gold Films on Silicon Wafers," http://www.ucl.ac.uk/~ucapikr/projects, (Mar. 31, 2009).

Bechelany et al. "Synthesis Mechanisms of Organized Nanoparticles: Influence of Annealing Temperature and Atmosphere," Crystal Growth and Design, vol. 10, pp. 587-596, (Oct. 21, 2010).

Niwa, O. et al., "Fabrication and characteristics of vertically separated interdigitated array electrodes," Journal of Electroanalytical Chemistry and Interfacial Electrochemistry, vol. 267, pp. 291-297, (Aug. 10, 1989).

Park, S.J. et al., "Array-Based Electrical Detection of DNA with Nanoparticle Probes," Science, vol. 295, pp. 1503-1506, (Feb. 22, 2002).

Urban, M. et al., "A paralleled readout system for an electrical DNA-hybridization assay based on a microstructured electrode array," Review of Scientific Instruments, vol. 74, pp. 1077-1081, (Jan. 2003).

Choi Y.S. et al., "Hybridization by an Electroatomical Genome on Detection on Using an Indicator-Free DNA on a Microelectrode-array DNA Chip" Bulletin of the Korean Chemistry Society, vol. 26, pp. 379-383, (2005).

Park, C.W. et al., "Fabrication of Poly-Si/ AU Nano-gaps Using Atomic-layer-deposited $Al_2O_3$ as a Sacrificial Layer," Nanotechnology, vol. 16, pp. 361-364, (Feb. 1, 2005).

Ruttkowski, E. et al., "CMOS based Arrays of Nanogaps Devices for Molecular Devices" Proceedings of 2005 5th IEEE Conference on Nanotechnology, vol. 1, pp. 438-441, (Jul. 2005).

Stagni, C. et al., "CMOS DNA Sensor Array with Integrated A/D Conversation Based on Label-Free Capacitance Measurement" IEEE Journal of Solid-State Circuits, vol. 41, pp. 2956-2964, (Nov. 20, 2006).

Schrott, W. et al., "Metal Electrodes in Plastic Microfluidic Systems" Microelectronic Engineering, vol. 86, pp. 1340-1342, (Jun. 2009).

Roy, S. et al., "Mass-Produced Nanogap Sensor Arrays for Ultra-Sensitive Detection of DNA," Journal of the American Chemical Society, vol. 131, pp. 12211-12217, (Aug. 5, 2009).

Choi, J. E. et al., "Fabrication of Microchannel with 60 Electrodes and Resistance Measurement" Flow Measurement and Instrumentation, vol. 21, pp. 178-183, (Sep. 2010).

Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).

Chen, X. et al., "Electrical Nanogap Devices for Biosensing," Materials Today, vol. 13, pp. 28-41, (Nov. 2010).

Ghindilis, A. et al., "Real Time Biosensor Platforms Fully Integrated Device for Impedimetric Assays," ECS Transactions, vol. 33, pp. 59-68, (2010).

Su, Y., "Modeling and Characteristic Study of Thin Film Based Biosensor Based on COMSOL," Mathematical Problems in Engineering, Article 581063 (6 Pages), (Apr. 7, 2014).

Blossey, R., "Self-Cleaning Surfaces—Virtual Realities," Nature Materials, vol. 2(5), pp. 301-306, (May 2006).

Cassie, A.B.D. et al., "Wettability of Porous Surfaces," Transitions of the Faraday Society, vol. 40, pp. 546-551, (Jan. 1944).

Choi, C. et al., "Strongly Superhydrophobic Silicon Nanowires by Supercritical CO2 Drying," Electronic Materials Letters, vol. 6 (2), pp. 59-64, (Jun. 2010).

Coulson S.R. et al., "Super-Repellant Composite Fluoropolymer Surfaces," The Journal of Physical Chemistry B., vol. 104(37), pp. 8836-8840, (Aug. 2000).

Gapin, A.I. et al., "CoPt patterned media in anodized aluminum oxide templates," Journal of Applied Physics, vol. 99(8), pp. 08G902 (1-3), (Apr. 2006).

(56) References Cited

OTHER PUBLICATIONS

Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010).
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Sc ience, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-523, (May 10, 2016).

\* cited by examiner

SEQUENCE LISTING

```
<160> NUMBER OF SEQ ID NOS: 15

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5ThioMC6-D (5'-thiol modifier)
```

-continued

<400> SEQUENCE: 1
tgcgtacgta tgtcatgaat ggcgcagact gatgtcctat gacgtcgcta ctgcagtact    60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5ThioMC6-D (5'-thiol modifier)
<220> FEATURE:
<221> NAME/KEY: modified_base
<222> LOCATION: (29)..(29)
<223> OTHER INFORMATION: iBiodT (internal biotin-modified
      deoxythymidine)

<400> SEQUENCE: 2
agtactgcag tagcgacgtc ataggacatc agtctgcgcc attcatgaca tacgtacgca    60

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met His Gly Lys Thr Gln Ala Thr Ser Gly Thr Ile Gln Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ser Gly Ser Ser Pro Asp Ser
1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Lys Ala His Leu Pro Pro Ser Arg Leu Pro Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Pro Ser Ser Gly Pro Gln Asp Thr Arg Thr Thr
1               5                   10

```
<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Ser Pro His Pro His Pro Arg His His His Thr
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ala Ala Ala Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Ala Ala Ala Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Glu Glu Glu Arg Arg Arg Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Glu Glu Glu Lys Lys Lys Lys
1               5

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine
<220> FEATURE:
<221> NAME/KEY: modified_base
<222> LOCATION: (19)..(19)
<223> OTHER INFORMATION: 5-methylcytosine
<220> FEATURE:
<221> NAME/KEY: modified_base
<222> LOCATION: (21)..(21)
<223> OTHER INFORMATION: 5-methylcytosine
<220> FEATURE:
<221> NAME/KEY: modified_base
<222> LOCATION: (23)..(23)
<223> OTHER INFORMATION: 5-methylcytosine

<400> SEQUENCE: 12
nnnnnnnnnn nnngcgcgcg cgcgcgcgcg cgcg                               34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(34)
<223> OTHER INFORMATION: a, c, t, g, unknown or other

<400> SEQUENCE: 13
cgcgcgcgcg cgcgcgcgcg cnnnnnnnnn nnnn                               34

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgccgcggag ccaagaaaaa aaaaaaaaaa aaaaattgca tgtcctgtga              50

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcacaggaca tgcaa                                                    15
```

BIOMOLECULAR SENSORS AND METHODS

CROSS-REFERENCE TO RELATED APPLICATIONS

This application is a continuation of International Application No. PCT/US16/39446 filed on Jun. 24, 2016, entitled "BIOMOLECULAR SENSORS AND METHODS" which claims priority to U.S. Provisional Patent Application No. 62/184,776 filed on Jun. 25, 2015, entitled "METHODS, COMPOSITIONS, APPARATUS AND MANUFACTURING METHODS OF MOLECULAR ELECTRONIC SENSORS," the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Oct. 27, 2016, is named 68952_00193_SL.txt and is 4,467 bytes in size.

FIELD

The present disclosure relates to electronic sensor devices. In particular, the disclosure relates to electronic sensor devices that comprise one or more biomolecule components in a measurement circuit.

BACKGROUND

Measuring properties at the molecular scale presents numerous challenges, due to the sensitivity required, and the presence of many potential sources of noise. In describing sensors for this purpose, it is therefore helpful to be clear about all sources of measurement error. In general, for any system or object that may be measured, a measured state, m, will only be an approximation of the actual system state, a. This may be due to any of a number of factors, such as imperfect signal interpretation reflecting error due to the operation of the sensor, the readout process, or the signal interpretation, and also because contacting the sensor to the system in some cases may perturb the state of the system. That the measured state m is different than the actual state a reflects the measurement error of the combined sensor, readout, and interpretation. Ideally, a sensor system will be constructed to make this measurement error as small as possible.

To measure states at a molecular scale, such as in the case of sequencing a DNA molecule, various efforts have been directed to creating sensor systems in which the sensor device has a "probe" that contacts the molecules of interest, preferably on a single-molecule scale, while other features of the sensor device are on larger nano- or micro-scales for purposes of manufacturing the sensor devices or integrating them into a signal transduction system.

In particular, a biosensor is an analytical device that functionally integrates a biological recognition component into a signal transduction system, to measure properties of biologically relevant molecules, such as DNA, RNA or proteins. That integration provides rapid and convenient conversion of biological events to detectable electrical signals. Of the various electrical biosensing architectures that have been devised, systems based on field-effect transistors (FETs) appear promising because they can directly translate interactions between target molecules (e.g., biological molecules) and the FET surface into detectable electrical signals. In a typical FET device, current flows along a channel that is connected to two electrodes (also referred to as the source and the drain). The channel conductance between the source and the drain can be modulated by a third electrode (also referred to as the gate) that is capacitatively coupled to the channel through a thin dielectric insulating layer. FETs can be used to detect target chemicals and measure chemical concentrations for a wide range of commercial applications. A classical and widely used example is a FET-based pH sensor, used to measure hydrogen ion concentration. This was introduced by Bergveld in the 1970's, and is used in solid-state pH sensors. The general field of ion-sensitive FET (ISFET) devices expands upon that concept for other chemical concentration measurements.

A limitation of current FET-type biosensor systems is their sensitivity. Current biosensor systems are unable to perform single molecule detection and identification. Likewise, they are unable to monitor single molecule reaction dynamics. These sensitivity limitations of FET-type biosensors prevent their use as detectors in important biochemical assays, such as in single molecule sequencing reactions.

Some efforts to improve FET biosensor sensitivity have focused on use of carbon nanostructures, such as carbon nanotubes, to form the channel between electrodes. However, carbon nanostructures pose various obstacles with respect to biosensor functionalization. In particular, there is no way to engineer in attachments sites at specific, desired atomic locations, for the purpose of attaching functional or sensitizing probe molecules. Additionally, present limits on precision, control, and scale of the synthesis of carbon nanostructures pose further challenges with respect to sensitivity and reliable production of individual sensors, establishing high density scalable arrays of sensors, and commercial viability of sensor manufacturing. Current carbon nanotube synthesis methods typically produce structures on a scale of around 100 nm or longer in length, a scale that is likely to pose limitations with respect to sensitivity as well as sensor density on a multi-sensor platform.

Thus, molecular-scale electronic biosensor devices with architectures compatible with increased sensitivity and precision, reliable engineering, and that are further compatible with efficient and commercially-viable manufacturing methods for achieving increased sensor density on a multi-sensor platform, are desirable. Likewise, improved methods of manufacturing such sensor devices are also desirable.

SUMMARY

The present disclosure generally relates to sensors, systems including the sensors, and to methods of forming and using the sensors and systems. Exemplary sensors can be used to, for example, sequence molecules such as DNA, RNA, or other oligonucleotides. While the ways in which various embodiments of the disclosure address the drawbacks of the prior art sensors are discussed in more detail below, in general, the disclosure provides sensors that are relatively easy and inexpensive to manufacture.

In accordance with various embodiments of the disclosure, a sensor includes a first contact coupled to a first electrode, a second contact coupled to a second electrode, a sensor gap defined between one of the first contact and the first electrode and one of the second contact and the second electrode, and a bridge molecule comprising a first end and a second end, wherein the bridge molecule is coupled to the first contact at the first end and coupled to the second contact at the second end. In accordance with various aspects of these embodiments, the bridge molecule is a biopolymer, or the bridge molecule is chemically synthesized. In accordance with additional aspects, the sensor includes a third or gate electrode. In these cases, the gate electrode can be used to tune and/or activate the sensor device. In accordance with further aspects, the sensor gap has a sensor gap dimension of between about 5 nm and about 30 nm. In accordance with additional aspects, the first end or the bridge molecule comprises a first self-assembling anchor; in accordance with further aspects, the second end comprises a second self-assembling anchor. Exemplary bridge molecules can include one or more of the following attributes: the bridge molecule can be linear (e.g., a linear biopolymer), the bridge molecule has an end-to-end length that is less than a persistence length of the bridge molecule, and the bridge molecule includes an end-to-end length configured to approximate the dimension of the sensor gap. Exemplary sensors include a probe attached to the bridge molecule. The probe can be configured to engage a single target molecule. Exemplary probes can include or be an enzyme configured to engage the target molecule during a reaction in a solution.

In accordance with additional embodiments of the disclosure, a sensor includes a first electrode overlying a substrate surface, a second electrode overlying a substrate surface, a sensor gap defined between the first electrode and the second electrode (or between contacts attached to the electrodes), and a bridge molecule comprising a first end and a second end, wherein the bridge molecule is coupled to a first contact at the first end and coupled to a second contact at the second end. The sensor gap can include a sensor gap dimension of between about 5 nm and about 30 nm. In accordance with various aspects of these embodiments, the bridge molecule is a biopolymer, or the bridge molecule is chemically synthesized. In accordance with additional aspects, the sensor includes a third or gate electrode. In these cases, the gate electrode can be used to tune and/or activate the sensor device. In accordance with additional aspects, the first end or the bridge molecule comprises a first self-assembling anchor; in accordance with further aspects, the second end comprises a second self-assembling anchor. Exemplary bridge molecules can include one or more attributes noted herein. Exemplary sensors include a probe attached to the bridge molecule. The probe can be configured to engage a single target molecule. Exemplary probes can include or be an enzyme configured to engage the target molecule during a reaction in a solution.

In accordance with additional exemplary embodiments, a system includes a sensor as described herein. The system can additionally include one or more circuits, such as a circuit formed using a substrate used to form the sensor or upon which the sensor resides. Systems can additionally or alternatively include additional circuits and/or devices to, for example, remove noise from a signal and/or assist with interpretation of the signal.

In accordance with yet additional embodiments of the disclosure, a method includes providing a sensor, such as a sensor described herein; contacting a nucleic acid template with a polymerase, wherein the polymerase is coupled to a bridge molecule comprising a portion of a sensor; providing a nucleotide base mix; performing, by the polymerase, an incorporation event comprising incorporation of a nucleotide from the nucleotide base mix into a synthesized nucleic acid; and detecting a signal produced by the incorporation event. In accordance with various aspects of these embodiments, a method can additionally include a step of applying an electrical potential to the sensor—e.g., to tune or activate the sensor. In accordance with further aspects, noise can be removed from the signal.

In accordance with yet additional embodiments, a method of manufacturing a biomolecular sensing device includes the steps of forming a first electrode and a second electrode on a substrate surface, wherein the first electrode and the second electrode are separated by an electrode gap; placing a first contact on the first electrode and a second contact on the second electrode, wherein the first contact and the second contact are separated by a contact gap; and attaching a bridge molecule to the first contact and the second contact. Exemplary methods can further include the step of contacting the bridge molecule with a probe to couple the probe to the bridge molecule.

And, in accordance with further embodiments of the disclosure, a method of sequencing an oligonucleotide comprises using one or more sensors as described herein.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments, a single molecule biosensor device can comprise a first electrode and a second electrode. The first electrode and the second electrode are separated by a sensor gap defined by the electrodes and/or contacts attached to the electrodes. The first and second electrodes can be coupled by a bridge molecule spanning the sensor gap. The bridge molecule can comprise a biopolymer, such as nucleic acid or amino acid polymers. The bridge may also comprise a chemically synthesized molecule, which may include a synthetic organic molecule, a polymer comprising synthetic analogs of biopolymer monomers, or other wholly synthetic monomers not derived from a biological molecule. A bridge molecule, whether comprised of a biopolymer or a synthetic molecule, may have a known, atomically precise molecular structure. The bridge molecule attachment to the electrodes may be mediated by a contact. A probe molecule or molecular complex can be coupled to the bridge molecule. The probe can be a biomolecule such as an enzyme configured to interact with a single target molecule. In various embodiments, a sensor device can comprise multiple single molecule biosensors arrayed in parallel. Such multi-sensor devices can be used to perform parallel detection, discrimination, and/or characterization or identification of multiple individual target molecules in a complex mixture of target and other molecules.

Figure 1:
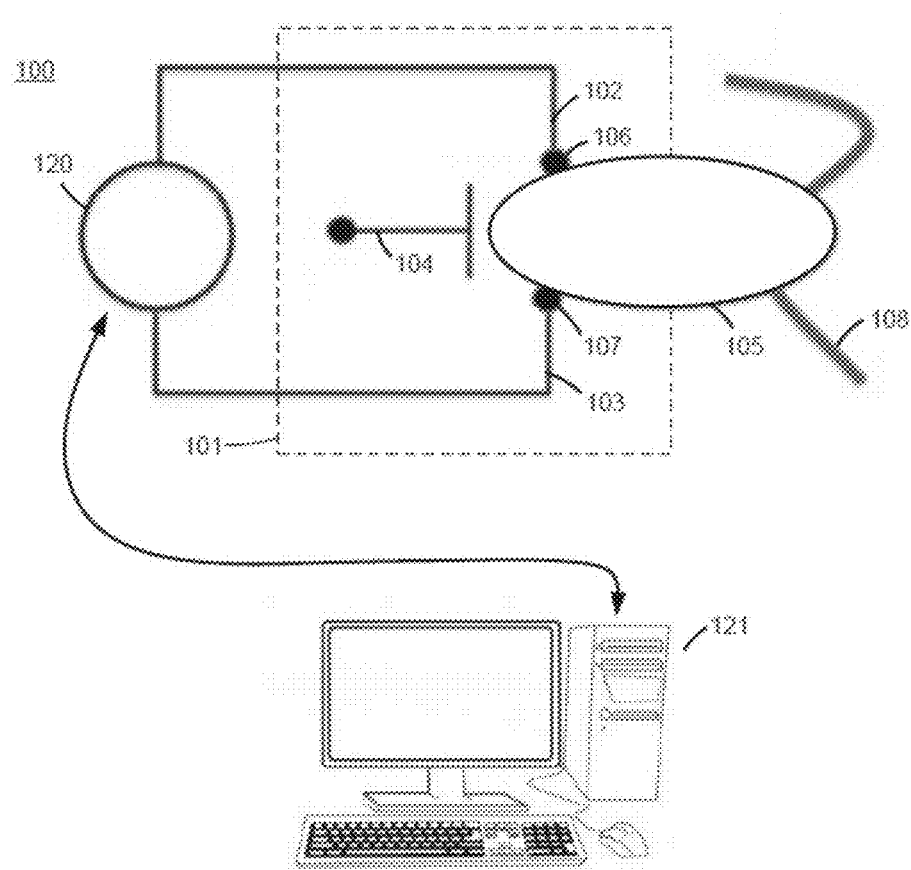
FIG. 1 illustrates a schematic representation of a sensor in accordance with various embodiments.
Figure 1:
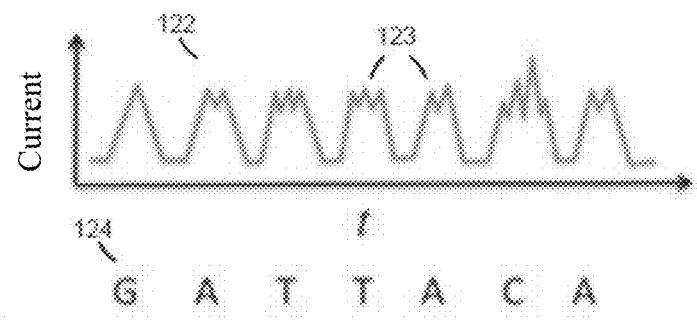

FIG. 1 illustrates a schematic representation of a sensor device 100 comprising a sensor 101 in accordance with various embodiments. Sensor 101 includes a first electrode 102 and a second electrode 103. Sensor 101 may also include a gate 104, as described in greater detail below. Sensor 101 can further comprise a sensor complex 105 functionally coupled to the first electrode 102 and the second electrode 103. In various embodiments, the sensor complex may be coupled to the electrodes via first contact 106 and second contact 107 attached to the respective electrodes. Sensor complex 105 can comprise multiple components, such as a bridge molecule and a probe molecule, as described in greater detail below. Sensor complex 105 can interact with the surrounding environment, thereby enabling sensor 101 to perform a sensing function. For example, as illustrated in FIG. 1, sensor complex 105 may interact with a target molecule 108 such as a DNA molecule, and the sensor device can be used to detect the presence of and/or properties of the target molecule.

In various embodiments, sensor device 100 and sensor 101 may be operatively connected to circuit 120 to detect a change of an electrical property of sensor 101. Circuit 120 is preferably an integrated circuit with micro-scale proximity to the sensor 101, but circuit 120 could also be embodied as an external electrical meter, such as a bench-top current meter. Sensor device 100 can comprise a plurality of sensors 101. Integrated circuit 120 can comprise a circuit architecture that may be fabricated using CMOS fabrication methods. Integrated circuit 120 can comprise an electronic measurement circuit for each sensor 101 that is fabricated within the same chip that provides support for the sensor. Expressed differently, a sensor device 100 can comprise a sensor 101 and an integrated circuit 120 in an integrated microcircuit. Integrated circuit 120 can further comprise readout circuitry and input/output features for connection to an external signal processing system 121.

In various embodiments, use of an integrated circuit 120 residing on a common semiconductor chip with sensor 101 can reduce sources of electronic noise in readings that can be produced by macroscopic, external circuit elements. For example, such a circuit may be a mixed signal CMOS sensor, comprising a small number of transistors, in the range of 1 to 200 depending on the performance requirements for sensitivity and readout. Such a circuit can function to measure current in a single sensor 101 in various embodiments. Further, a sensor device 100 can comprise an integrated circuit 120 comprising sensor/readout circuits for an array of sensors 101 so as to support the simultaneous operation of a large number of sensors in contact with the same sample.

In various embodiments, a sample contacted by a sensor 101 will comprise a liquid-phase sample. The solution comprising the sample may be extremely dilute and at low ionic strength to reduce the noise in electrical measurements performed using the sensor. The acquired signal will typically be the current flowing between electrodes 102 and 103 in the sensor, although it could be a related observable electronic parameter such as the voltage between electrodes, resistance/conductance between electrodes, or gate voltage.

In various embodiments, the configuration of sensor 101 and integrated circuit 120 in an integrated microchip chip format amenable to fabrication using modern CMOS fabrication methods can facilitate production of sensor devices with a highly compact architecture. In various embodiments, the integrated circuit for a sensor may be located within about 100 µm of the sensor gap, or within about 50 µm of the sensor gap, or within about 20 µm of the sensor gap, or within about 10 µm of the sensor gap, or within about 5 µm of the sensor gap, or within about 1 µm of the sensor gap. Moreover, in various embodiments, a sensor device can comprise a plurality of sensors, each sensor having an associated integrated circuit located within the parameters specified above.

Signal processing system 121 can be configured to provide electronic control of sensor device 100 and to receive, store, and analyze signal received from the sensor device and each sensor 101 therein. Signal processing system 121 can comprise a computer system with a processor and/or software configured to perform the electronic control functions, including control of the voltage and current applied to each sensor 101, and to perform the signal processing functions for signal received from each sensor 101.

For example and as illustrated in FIG. 1, a sensor device 100 comprising a sensor 101 may be used to perform a nucleic acid sequencing reaction. During operation of the device, a voltage may be applied between the first electrode and the second electrode of sensor 101, with interactions of the sensor with a target producing modulation of current flow through a biopolymer bridge molecule (see, e.g., 333, FIG. 3) that can be measured using integrated circuit 120 and signal processing system 121. Sensor 101 may produce a signal pattern 122 over time t with signal features 123 produced by the sensor in response to the sensor complex interaction with features of target molecule 108. Signal processing system 121 can receive and process the signal pattern and provide a sequence output 124 in response to the signal pattern, which in this context is the interpretation of the signal.

In various embodiments, a single molecule biosensor can take the form of a transistor, such as a field effect transistor (FET), with the attached bridge molecule and/or probe, and/or target molecule and/or solution-phase molecules in close proximity to these components, serving as a channel or conductive path in an electrical circuit. In such an embodiment, a sensor complex comprising a single probe molecule may be configured to bind or interact with a single target molecule as explained in greater detail below, thereby providing the biosensor with single molecule sensitivity. Such a transistor embodiment may include a two or three terminal transistor, or potentially more terminals, such as in the case of multi-gate devices.

Figure 2A:
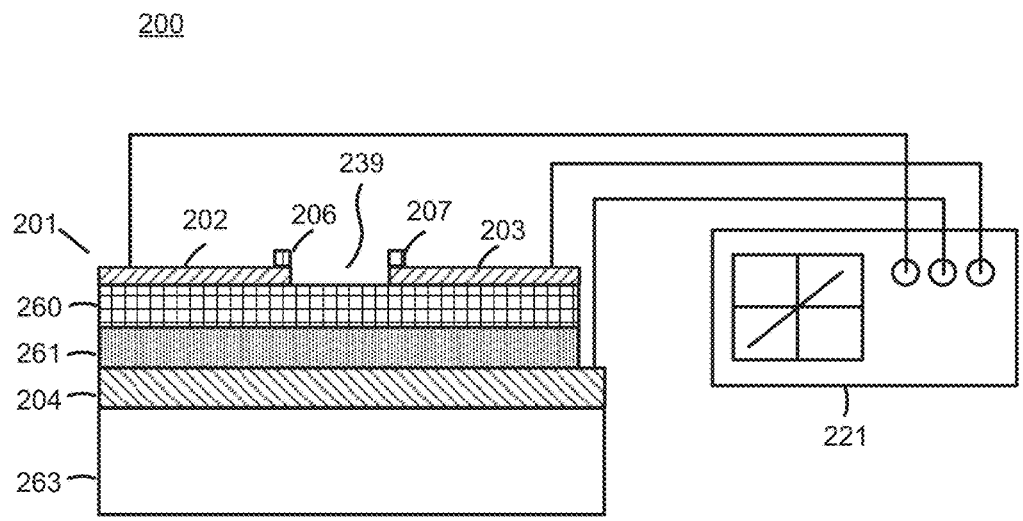
FIGS. 2A and 2B illustrate views of a sensor device in accordance with various embodiments.
Figure 2B:
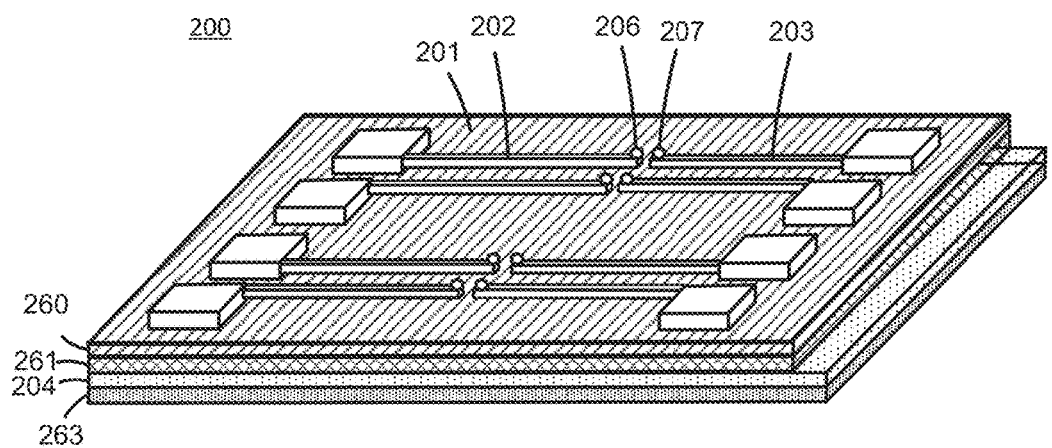

FIGS. 2A and 2B illustrate views of a sensor device 200 in accordance with various embodiments. Sensor complexes are not shown in the illustrated views of sensor device 200. Sensor device 200 comprises a plurality of sensors 201, with each sensor comprising a first electrode 202 and a second electrode 203. Each sensor can further comprise a sensor gap 239. In the illustrated embodiment, each sensor comprises a first contact 206 attached to the first electrode and a second contact 207 attached to the second electrode. In various embodiments, the electrodes can be disposed on a semiconductor substrate surface. For example, sensor device 200 can comprise a silicon nitride layer 260 overlying a silicon dioxide layer 261. Sensor device 200 can further comprise buried gate 204 underlying the semiconductor substrate layer(s) on which the electrodes are disposed. The various components described above can be fabricated on a support such as a silicon chip 263. As illustrated schematically in FIG. 2A, each of the first electrode 201, the second electrode 202, and the gate 204 may be connected to a signal processing system 221, which may be an external meter, as depicted in the illustration, but which could alternatively be integrated circuitry (details not shown).

Figure 3:
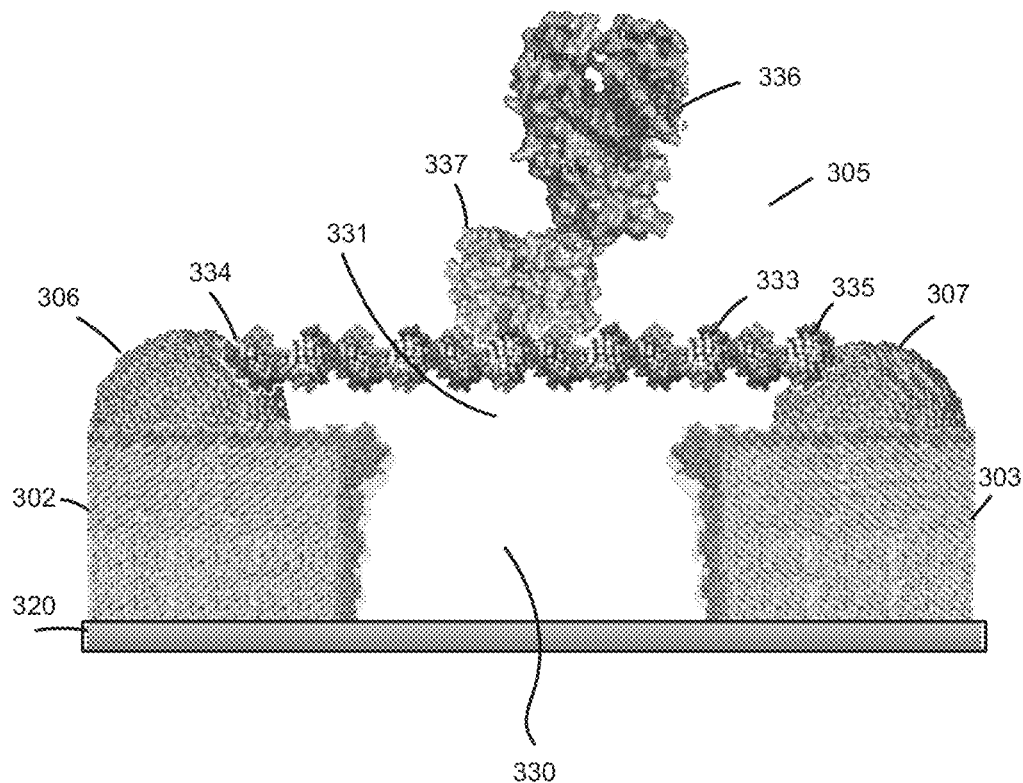
FIG. 3 illustrates a profile view of a portion of a sensor in accordance with various embodiments.

With reference now to FIG. 3, a profile view of a portion of a sensor 301 and sensor complex 305 are illustrated in greater detail. Sensor 301 comprises first electrode 302 and second electrode 303. First electrode 302 and second electrode 303 may be disposed on a substrate 320. In various embodiments, sensor 301 can further comprise a first contact 306 and a second contact 307 operatively coupled to first electrode 302 and second electrode 303, respectively. However, contacts are not strictly required, and a sensor in accordance with the present disclosure need not comprise a first and second contact. The ends of first electrode 302 and second electrode 303 define an electrode gap 330. Likewise, for a sensor comprising contacts such as sensor 301, the distance between first contact 306 and second contact 307 defines a contact gap 331. The actual dimension of a contact gap for any given first contact and second contact may vary dependent on the configuration of the contact and the point of the contact used for reference. For example, for the hemispherical first contact 306 and second contact 307 illustrated in FIG. 3, the dimension of contact gap 331 may be measured between the nearest points of the contact or from center to center. In various embodiments, one of the electrode gap and the contact gap, or the gap defined collectively or by various combinations of the electrodes and/or contacts, may be referred to as a sensor gap.

With continued reference to FIG. 3, sensor 301 further comprises sensor complex 305. In various embodiments, a sensor complex 305 can comprise a bridge molecule 333 and a probe 334. Probe 334 can be coupled to bridge molecule 333 via a linker 337, which here is shown as a streptavidin-biotin complex, with the biotin covalently incorporated into a nucleotide of the DNA bridge 333, and the streptavidin chemically, covalently cross-linked to the polymerase 334. Each of the various components of sensor complex 305 are described in greater detail below.

In various embodiments, a bridge molecule 333 can comprise a chemically synthesized bridge molecule or a biopolymer bridge molecule. A chemically synthesized bridge molecule or a biopolymer bridge molecule may be configured to span a sensor gap both structurally and functionally. For example, a chemically synthesized molecule or biopolymer molecule may be configured through selection and use of atomically precise molecular subunits (e.g., monomeric units for incorporation into a polymeric bridge molecule) that provide for construction of a bridge molecule with known or predictable structural parameters, incorporation of features that facilitate self-assembly to contact points and self-assembly of a probe molecule to a bridge molecule, as well as suitable electrochemical properties for electrical connection of electrodes.

Figure 21:
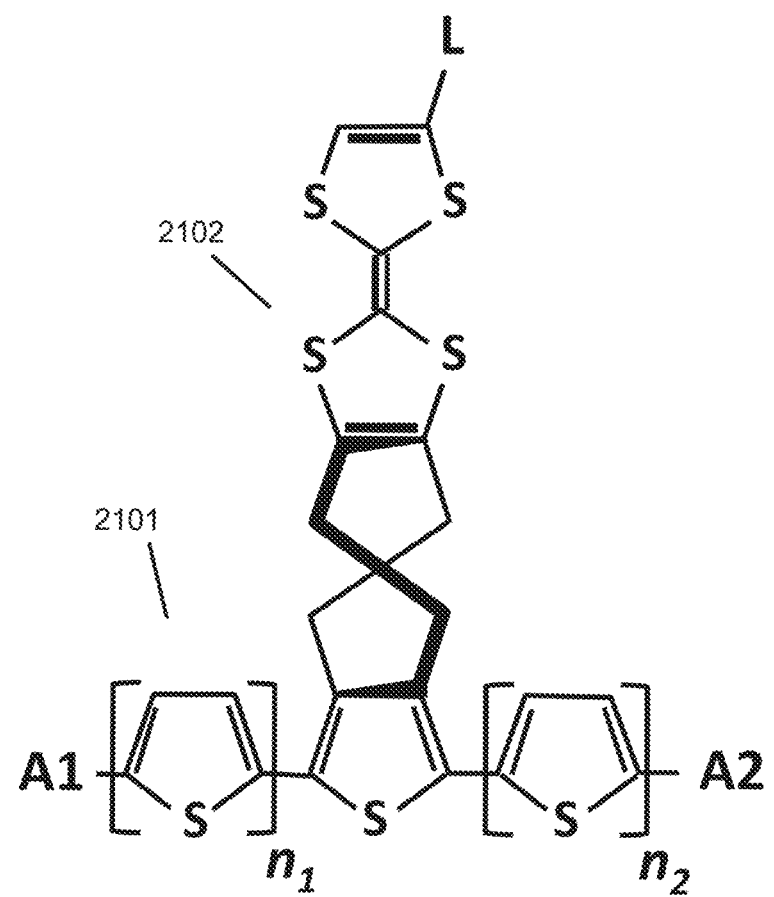
FIG. 21 illustrates a chemically synthesized bridge molecule in accordance with various embodiments.

A chemically synthesized bridge molecule is a molecule that can be assembled by a person of skill in the art of synthetic organic chemistry. For example, a chemically synthesized molecule can comprise a poly pyrrole, polyaniline, or polythiophene backbone. With reference briefly to FIG. 21, an example of a general structure of a polythiophene-based chemically synthesized bridge molecule 2100 is illustrated. Chemically synthesized bridge molecule 2100 can comprise a chain of thiophene rings 2101 forming the backbone of the bridge molecule, with $n_1$ and $n_2$ thiophene rings on either side of a probe support moiety 2102 that may be configured at a specific location in the bridge molecule 2100. Since each thiophene ring 2101 is approximately 0.3 nm wide, a chemically synthesized bridge molecule comprising about 10 to about 100 rings could be constructed to span an about 3 nm to an about 30 nm gap. The termini (e.g., A1 and A2) of a chemically synthesized bridge molecule can comprise thiol or amine groups, or other groups configured to bind to electrode or contact materials. A chemically synthesized bridge molecule can also be configured with a linker (e.g., L) suitable to provide attachment of a probe molecule. Any other chemically synthesized bridge molecule configuration, comprised of any suitable backbone moiety now known to, or that may be hereinafter devised by, a person of ordinary skill in the art, may be used in accordance with various embodiments of the present disclosure.

As used herein, the term "biopolymer" can include any molecule comprising at least one monomeric unit that can be produced by a living organism, although the actual monomeric unit comprising a biopolymer or the polymer itself need not be produced by an organism and can be synthesized in vitro. Examples of biopolymers include polynucleotides, polypeptides, and polysaccharides, including well known forms of these such as DNA, RNA and proteins. Bridge molecules that comprise a biopolymer can include multi-chain polymeric proteins in a simple "coiled-coil" configuration, as occurs in collagen proteins, or a more complex folding of heavy and light chain polymeric proteins, such as in immunoglobin molecules (e.g. IgG). Such complexes that comprise biopolymers also include common nucleic acid duplex helices, such as a DNA double helix, which is two DNA single strand molecules bound into a helical double strand by hydrogen bonding, PNA-PNA duplexes, as well as DNA-RNA, DNA-PNA, and DNA-LNA hybrid duplexes. A biopolymer molecule need not be naturally occurring or produced by an organism to be classified as a biopolymer. Instead, for purposes of the present disclosure, the term "biopolymer" can include molecules that are synthesized enzymatically as well as non-enzymatically and can likewise include molecules comprising synthetic analogues of naturally-occurring monomeric units. For example, biopolymers can comprise peptide nucleic acids (PNAs) and locked nucleic acids (LNAs), synthetic analogues of DNA and RNA that have enhanced stability properties. In addition, a biopolymer can comprise any of a variety of modifications that may be added to a molecule. The use of biopolymer bridge molecules can provide various benefits, including synthesis of precisely controlled structures having suitable size and chemistry for sensor function, they may be naturally compatible with the target molecules for the sensor (e.g., compatible with the same liquid buffer medium), and the biotech industry has developed extensive capabilities to design, engineer and synthesize such molecules, and to manufacture them economically and with high quality control.

A bridge molecule can be configured to span a sensor gap and be coupled to an electrode and/or a contact on either side of the sensor gap in a manner suitable to provide electronic communication between the bridge molecule and the electrode and/or contact.

In various embodiments, a bridge molecule can comprise a linear biopolymer such as a double-stranded DNA helix or an α-helical polypeptide. As illustrated in FIG. 3, bridge molecule 333 comprises a linear biopolymer double-stranded DNA bridge molecule with a first end 334 coupled to first contact 306 and a second end 335 coupled to second contact 307.

In various embodiments, a rigid bridge structure may provide advantages in terms of taking on a well-defined configuration during and after assembly of the sensor complex. Without wishing to be bound by theory, a linear biopolymer can comprise a semi-flexible polymer that may be described by its bending rigidity. On a short length scale, a linear biopolymer may behave as a rigid polymer, requiring a strong force to bend the polymer, while on a longer scale, the linear biopolymer may be bent or curved more easily. The characteristic bending length measure within which a linear biopolymer essentially behaves as a rigid molecule in a certain set of environmental conditions is referred to as the persistence length. The persistence length can depend on the environmental conditions in which a bending force is exerted on the polymer, with variables such as the temperature and ionic conditions of the surrounding environment affecting the persistence length. The persistence length of a linear biopolymer such as double-stranded DNA may be estimated based on theoretical modeling or it may be measured empirically for a set of environmental conditions corresponding to a predetermined experimental condition in which a device in accordance with various embodiments may be used. For example, the persistence length of double-stranded DNA has been calculated at about 30 nm to about 80 nm, and the persistence length of an α-helical peptide calculated at about 80 nm to about 100 nm in various conditions that may approximate the conditions in which a sensor in accordance with various embodiments of the present disclosure may be used. Thus, in various embodiments, a double-stranded DNA molecule or an α-helical peptide having an end-to-end length, as measured along its major axis, of less than the respective persistence length parameters described above may behave as an essentially rigid polymer, thereby providing certain advantages or benefits with respect to device assembly and performance.

In various embodiments, use of linear biopolymers comprised of DNA or amino acids permits the straightforward construction of nano-scale sensor components having a predetermined length based on the monomeric composition (i.e., the primary structure) of the biopolymer. Without wishing to be bound by theory, use of a linear biopolymer with an end-to-end length of less than the persistence length may enhance the efficiency of a self-assembly step during construction of a biomolecular sensing device in accordance with various embodiments. Use of such linear biopolymers provides an ability to maintain the specifications of a biopolymer bridge molecule within parameters in which their micromechanical properties are more predictable than for longer linear biopolymers that may bend or fold, thereby reducing the influence of undesirable stochastic effects, for example, during bridge molecule synthesis, handling, self-assembly, or sensor operation. Moreover, the use of linear biopolymers permits precise specification of the bridge molecule length to the sensor gap (i.e., the electrode gap and/or contact gap dimension and architecture), providing a further ability to readily test the performance of theoretical structural models and device improvements and to make incremental, well-controlled, and empirically-testable modifications. In various embodiments, a linear biopolymer bridge molecule may be configured to provide a reduced rate of miscoupling of both the first self-assembling anchor at the first and the second self-assembling anchor and the second end to one of the first contact and the second contact due to the essentially rigid nature of the linear biopolymer bridge molecule at the scale used in the sensor device (e.g., an end-to-end length of between about 5 nm and about 30 nm). Similarly, a biopolymer bridge molecule may be configured to provide a reduced rate of single-end coupling. This may result when the substantially rigid bridge molecule, once coupled at a first contact, restricts the second end to spend more time in the proximity of the desired second contact point, owing to the spacing of contacts, thereby increasing the rate of the desired second coupling reaction.

As mentioned above, a biopolymer bridge molecule can comprise a double-stranded DNA molecule. In various embodiments, a double-stranded DNA can comprise a thiol-modified oligo comprising a thiol-modified nucleotide or base. A thiol-modified nucleotide can comprise a self-assembling anchor configured to bind to a gold nanobead or similar surface contact. In various embodiments, a self-assembling anchor can comprise a 5'-thiol modified nucleotide, which can be located at or near the 5' terminus of an oligonucleotide. A double-stranded DNA molecule can comprise a complementary pair of oligonucleotides, with each oligonucleotide comprising a 5'-thiol modified nucleotide, such that the assembled double-stranded DNA comprises a self-assembling anchor located at both termini of a double-stranded DNA molecule. For example, in various embodiments, a double-stranded DNA molecule can comprises oligonucleotides with the following sequences:

```
                                    (SEQ ID NO: 1)
5'-/5ThioMC6-D/TGC GTA CGT ATG TCA TGA ATG GCG

CAG ACT GAT GTC CTA TGA CGT CGC TAC TGC AGT

ACT-3',
and (SEQ ID NO: 2)
5'-/5ThioMC6-D/AGT ACT GCA GTA GCG ACG TCA TAG

GAC A/iBiodT/C AGT CTG CGC CAT TCA TGA CAT ACG

TAC GCA-3',
``` with the "/5ThioMC6-D/" denoting a 5'-thiol modifier and "/iBiodT/" denoting an internal biotin-modified deoxythymidine nucleotide (Integrated DNA Technologies, Inc., Coralville, Iowa). When annealed to one another, these oligos provide a double-stranded DNA molecule with a 5'-thiol modified nucleotide located at each end of the molecule as the first and second self-assembling anchors.

A double-stranded DNA molecule bridge can also further comprise a biotin linker component to facilitate linking a probe molecule to the bridge with a complementary avidin-type linker component. In various embodiments and as illustrated in the reverse oligonucleotide sequence described above, a biotin-modified oligonucleotide can be incorporated into one of the oligos of a double-stranded DNA molecule bridge. In various embodiments, the biotin-modified oligo is an internal modification, such as via a modified thymidine residue (biotin-dT). A variety of biotin modification configurations may be used, including attachment to thymidine via a C6 spacer, attachment via a triethyleneglycol spacer, attachment via a photocleavable spacer arm, dual biotin modifications, desthiobiotin modifications, and biotin azide modifications. Other modifications that are now known to a person of skill in the art or may be hereinafter devised and may be made to an oligonucleotide to facilitate linkage to a probe molecule are within the scope of the present disclosure. Similarly, other common small molecules with a protein binding partner, such digoxigenin, can play a similar role to that of biotin for such purposes of conjugation to probe molecules at precisely atomically specified points in the bridge molecule.

In various embodiments, a peptide biopolymer bridge molecule can comprise various configurations and/or features suitable to provide various desirable bridge molecule structure and performance characteristics, including electrode or contact binding characteristics, structural characteristics, electrical performance characteristics, and the like. For example, a peptide biopolymer bridge can comprise an L-cysteine residue at one or both of the amino terminus and the carboxyl terminus to serve as a self-assembling anchor via thiol-metal binding to specific metal contacts that engage in strong thiol binding, such as gold, palladium or platinum. In other embodiments, a biopolymer bridge molecule can comprise a peptide with the known capacity to selectively and strongly bind gold contacts for purposes of self-assembly and electro-mechanical connection into the circuit. Specific such peptides include those with the following amino acid sequences: MHGKTQATSGTIQS (SEQ ID NO: 3), VSGSSPDS (SEQ ID NO: 4), and LKAHLPPSRLPS (SEQ ID NO: 5). Other peptides selected for such properties can similarly bind other specific metal or material contacts. For example, VPSSGPQDTRTT (SEQ ID NO: 6) is a known aluminum binding peptide, and MSPHPHPRHHHT (SEQ ID NO: 7) is a known silicon dioxide binding peptide. In various other embodiments, a biopolymer bridge molecule can comprise a peptide sequence that includes repetitions of an amino acid motif or motifs selected from one of the following amino acid sequence motifs known to favor the formation of stable alpha-helix conformations, providing for a linear, rigid, conductive bridge: EAAAR (SEQ ID NO: 8), EAAAK (SEQ ID NO: 9), EEEERRRR (SEQ ID NO: 10), and EEEEKKKK (SEQ ID NO: 11). Such a peptide biopolymer bridge molecule can also comprise a modified amino acid consisting of a lysine residue with a covalently attached biotin to provide a conjugation point at a precisely atomically defined location for avidin-based conjugation to probe molecule complexes. A modified lysine can replace a standard lysine or arginine residue in such a peptide sequence motif, to otherwise maintain or minimally alter the properties of the alpha-helix.

Figure 4:
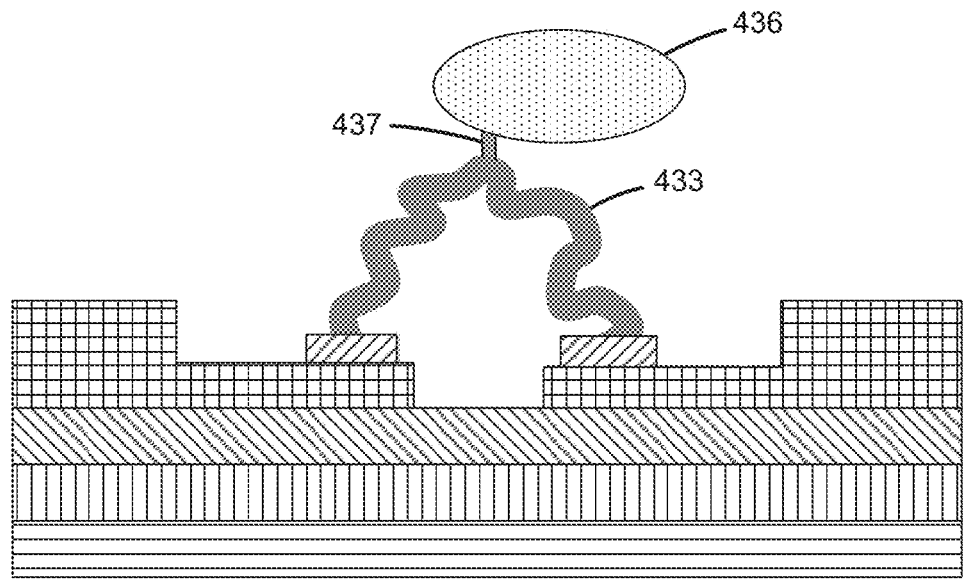
FIG. 4 illustrates a sensor comprising a biopolymer bridge molecule in accordance with various embodiments.
Figure 5:
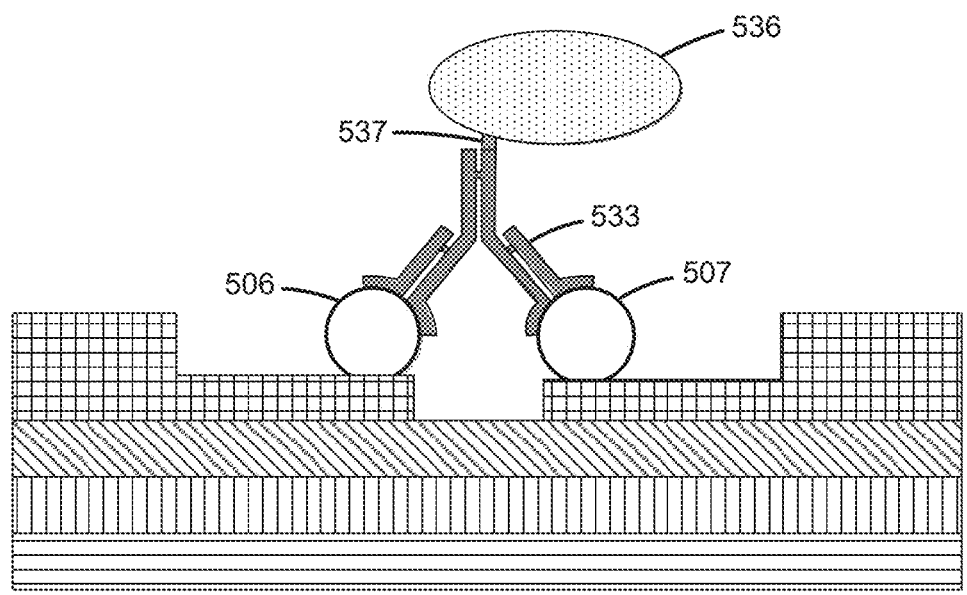
FIG. 5 illustrates a sensor comprising a biopolymer bridge molecule in accordance with various embodiments.

In various embodiments, a biopolymer bridge molecule can have other configurations. For example and as illustrated in FIG. 4, a biopolymer bridge molecule 433 can comprise a linear biomolecule that is flexed, folded, or comprises a certain degree of secondary structure. In various embodiments, a biopolymer bridge molecule can further comprise molecules having tertiary and/or quaternary structure, including globular proteins, antibodies, and multi-subunit protein complexes. An example is illustrated in FIG. 5, in which the biopolymer bridge molecule 533 comprises an immunoglobin G protein (IgG). In the illustrated embodiment, the electrical contacts (506, 507) are gold nanoparticles, and the IgG has been established with a specific affinity to bind such particles.

Similarly to sensor 301, the configurations illustrated in FIG. 4 and FIG. 5 each comprise a probe (436 and 536, respectively) coupled to the biopolymer bridge molecules via linkers (437 and 537, respectively). The illustrated embodiments are intended to exemplify the range of possible biopolymer bridge molecule configurations that may be couple to electrodes or contacts comprising different materials and configurations, including different metallic or nonmetallic conducting or semiconducting contacts in different structural configurations. In various embodiments, electrodes or contacts may further be coated, treated, or derivatized to facilitate bridge assembly and/or attachment using products such as InnovaCoat GOLD nanoparticles (Innova Biosciences).

A probe in accordance with various embodiments can comprise any suitable molecule or multicomponent molecular complex. A probe may be selected based on the molecule to be detected by the sensor or the biochemical reaction to be monitored. Various examples of probes include peptides, proteins, enzymes, nucleic acids, ribozymes, catalytic DNAs, and the like. In various embodiments, an enzyme can comprise a lysozyme, a kinase, or a polymerase. Any molecule or complex that exhibits a specific change in physical, chemical, or electronic configuration in response to binding or processing of a substrate or target molecule may be used as a probe in accordance with various embodiments of the present disclosure.

In various embodiments, a probe can comprise an enzyme such as polymerase or a reverse transcriptase suitable for interacting with individual DNA or RNA target molecules. Enzymes that catalyze the template-dependent incorporation of nucleotide bases into a growing oligonucleotide strand undergo conformational changes in response to sequentially encountering template strand nucleic acid bases and/or incorporating template-specified natural or analog bases (i.e., an incorporation event). Such conformational changes can modulate electrical current through a bridge molecule to which the probe is coupled, thereby provide a sequence-specific signal pattern in a manner that is dependent on the template molecule. As described above, the signal pattern may be detected by a signal processing system and translated to a sequence data output. Moreover, the presence of a modified nucleotide in a target nucleic acid sequence may produce unique conformational changes and corresponding signal features in a signal pattern that can enable a sensor device and signal processing system to directly determine, for example, methylation of bases in a target sequence on a base-by-base basis. Such a label-free, direct sequencing method may permit discrimination of a nucleotide-specific incorporation event in a sequencing reaction using nucleotide base mix comprising a mixture of natural and/or analog bases corresponding to all four bases of DNA, although a sequencing process comprising sequentially providing individual natural or analog bases in a serial and/or cyclic fashion may also be used. The use of a reverse transcriptase as the probe molecule can similarly enable the direct sequencing of RNA molecules without the need for an intermediate cDNA conversion step.

In various embodiments and as described briefly above, a probe can be attached to the bridge molecule via a self-assembling linker. A self-assembling linker can comprise any of a number of structures suitable to attach a first biomolecule to a second biomolecule. In various embodiments, a self-assembling linker can comprise a first linker component and a second linker component that is complementary to the first linker component. The first linker component and the second linker component may be joined by self-assembly to form an assembled linker based on an affinity of the first linker component for the second linker component. A first linker component can be associated, for example, with a bridge molecule, and a second linker component can be associated with a probe. A linker component associated with a bridge molecule can be engineered to a specific site in the bridge molecule, such that self-assembly of the probe to the bridge produces coupling of the probe to the bridge molecule at a predetermined location on the bridge molecule. A linker component selected for association with the probe may be configured to minimize interference between the probe and a target, both with respect to the size of the linker component and the position at which it is conjugated to the probe. In this manner, joining the complementary first and second linker components can provide functional attachment of the probe to the bridge molecule. A self-assembling linker can comprise a biotin-avidin coupling mechanism, with an avidin (or other avidin-like) protein first linker component and a biotin small molecule second linker component, which components form a strong non-covalent bond with one another. Other avidin-like proteins include streptavidin, rhizavidin, bradavidin, NeutrAvidin, other various amino-acid modified forms of avidin or streptavidin, as well as divalent or monomeric derivatives of such avidins which retain biotin-binding functionality. In various embodiments, for example, a biotin may be conjugated to the bridge molecule and a streptavidin conjugated to the probe molecule. A self-assembling linker can also comprise the well-known "click-chemistry" mechanisms for bioconjugation. A self-assembling linker can also comprise an antigen-antibody coupling, for example with an antigen present on the bridge molecule coupling to an antibody conjugated to the probe molecule. A self-assembling linker can also comprise, for example, a SpyCatcher peptide first linker component and a SpyTag peptide second linker component, with the two components binding to form an irreversible covalent bond. Any other self-assembling linker system in any configuration now known to, or that may be hereinafter devised by, a person of ordinary skill in the art may be used to couple a probe to a bridge molecule.

In various embodiments, a sensor need not comprise a probe molecule distinct from the bridge molecule. Instead, the bridge molecule itself may be configured to be acted on by a target molecule. For example, a bridge can comprise a protein binding site, such as a kinase binding site, and be used to detect the presence and/or activity of the corresponding protein in a sample based on binding of the target protein to the bridge and/or modification of the bridge by the target protein.

Figure 6A:
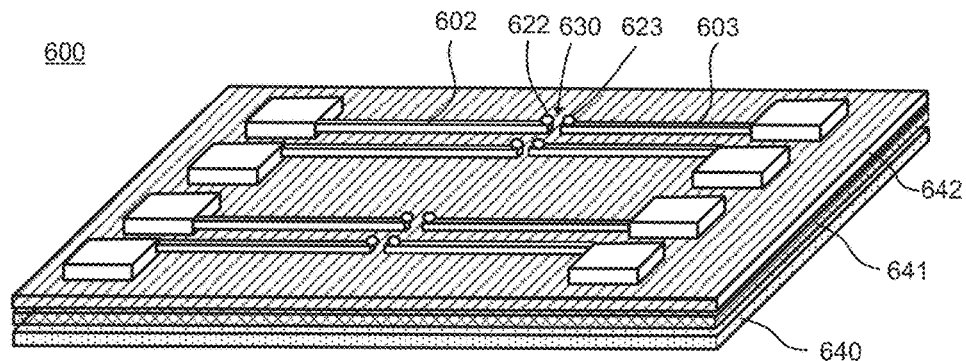
FIGS. 6A and 6B illustrate views of a sensor device in accordance with various embodiments.
Figure 6B:
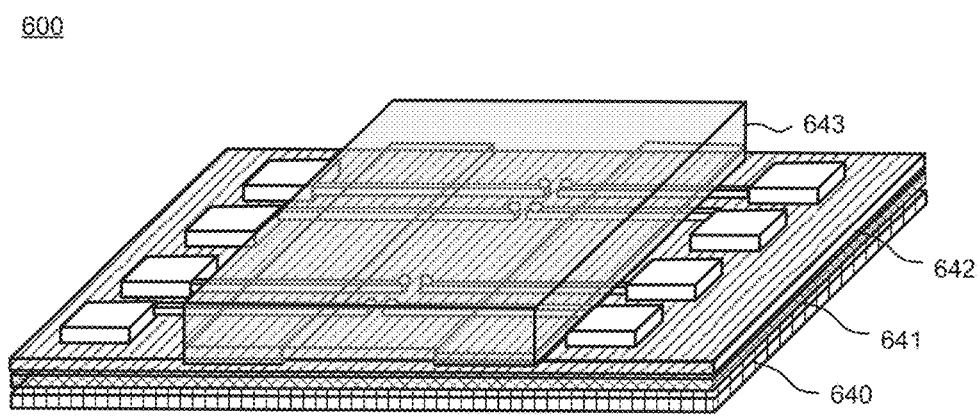

With reference now to FIGS. 6A and 6B, perspective views of a partially-fabricated sensor device 600 with and without a sensor enclosure are illustrated. Sensor device 600 is a three terminal sensor device comprising a buried gate 640. Device 600 illustrated in FIG. 6A comprises various features of a sensor device that may be produced using CMOS fabrication techniques, such as gate 640 underlying substrate 641 and oxide 642, along with first electrodes 602 and second electrodes 603 separated by electrode gaps 630, and each electrode having an attached contact 606/607. Attachment of the various sensor complex components described above, including a bridge molecule and probe, may be performed in downstream self-assembly steps. In various embodiments and as illustrated in FIG. 6B, sensor device 600 may first be configured with an enclosure 643 configured to enclose or form a flow cell around sensor gaps 630 prior to completing assembly of the sensors by contacting the sensor with a solution comprising the bridge and/or probe molecules. Likewise, enclosure 643 may also be used to perform assays such as sequencing reactions. Enclosure 643 can be separately formed and attached to a structure including device 600.

Biomolecule Detection and Nucleic Acid Base Discrimination

In various embodiments, a method for detecting the dynamics and kinetics of a single molecule sensing device such as device 100 (FIG. 1) is provided. Any method for measuring changes in electrical conductance of a sensor 101 comprising a bridge molecule can be used to monitor a sensor device described herein. In various embodiments, a voltage of less than about 10 V can be applied to a sensor comprising a biomolecular bridge molecule, and in various embodiments described in greater detail below, a voltage of about 0.5 V is applied. The current flowing through the sensor can be measured as a function of time using integrated circuit 120. Target binding and/or processing events by a probe (i.e., enzyme activity in the case of an enzymatic probe) in sensor complex 105 can produce changes to the conductivity of the sensor 101, modulating the measured current to produce a signal pattern 122 over time t comprising signal features 123. Such events, and the associated conformational changes, including structural, chemical, and electronic changes (i.e., charge distributions in an enzyme, substrates, and surrounding solution) can comprise kinetic features of target binding and processing, with the various events producing current fluctuations comprising signal features 123 that can be measured, recorded, discriminated, analyzed or stored using signal processing techniques which are known in the art. The signal features can comprise any of a range of possible forms, including wavelets with shapes that are triangular, sinusoidal, or have any number of Fourier components. For example, a polymerase used as a probe in a sensor can provide a polymerase kinetic signature for each discrete interaction with a template base (i.e., a target molecule feature) and/or a template-dependent nucleotide incorporation (i.e., the polymerase kinetic signature is template base-dependent), with a nucleic acid template target comprising a sequence of target molecule features at discrete positions in the target molecule (i.e., first, second, and nth target molecule features at first, second, and nth target molecule positions), each target molecule feature producing a corresponding signal feature during detection by a sensor in accordance with the present disclosure. The n target molecule features can correspond to n consecutive bases of a single stranded DNA template molecule (i.e., the target) which is processed by the polymerase enzyme to sequentially incorporate complementary nucleotides at these n target molecule features. The amplitudes, durations, and shapes of a signal pattern comprising a series of signal features can encode a target-specific sensor response that can be analyzed using signal processing system 121 to compare the signal pattern to a signal interpretation map to determine the identity of the target. Increasing the time resolution of signal detection and analysis may provide an ability to further resolve kinetic variability, transitions, and intermediate states of a probe-target interaction.

Since the fidelity of nucleotide incorporation is paramount to accurate nucleic acid sequencing, in various embodiments, a method of sequencing may rely on analog bases that increase the conformational changes of template-based nucleotide incorporation, thereby producing clearer signals, and/or otherwise provide an enhanced ability to discriminate incorporation of the analog base, thereby providing for enhanced sequencing accuracy. Non-labeled analog bases that can be used to enhance the kinetic or dynamic discrimination of template-dependent nucleotide incorporation are well known and can include modifications of the purine and pyrimidine bases and the deoxyribose or ribose and phosphate portions of a nucleotide. In particular, this can include adding additional groups to the gamma-phosphate of the nucleotide, which accepts large and diverse molecular modifications that are cleaved off during incorporation and therefore do not permanently impact the growing strand and its interaction with the polymerase.

In various embodiments, a method can provide detection of unmodified and modified nucleotide bases in a nucleic acid template sequence. For example, a method may be suitable to distinguish a modified template nucleotide, including $N^6$-methyladenosine, $N^4$-methylcytosine, 5-methylcytosine, 5-hydroxymethylcytosine, 5-formylcytosine, and 5-carboxylcytosine bases, as well as damaged template sequence positions such as abasic sites. Without wishing to be bound by theory, a DNA polymerase catalyzing incorporation of a nucleotide into a complementary nucleic acid strand during a sequencing reaction may exhibit differential polymerase kinetics in a manner dependent on the identity of the nucleotide in the template strand. Using devices and methods in accordance with the present disclosure, the identity of a nucleotide base in a nucleic acid template may be determined in near real-time based on detection of an electronic signature corresponding to the incorporation event. Unlike other systems and methods that rely on detection of a fluorescence signal associated with incorporation of a fluorophore-labeled nucleotide, fluorescence-based detection reagents and signal detection devices are not required, thereby reducing cost and complexity of the process.

Figure 7:
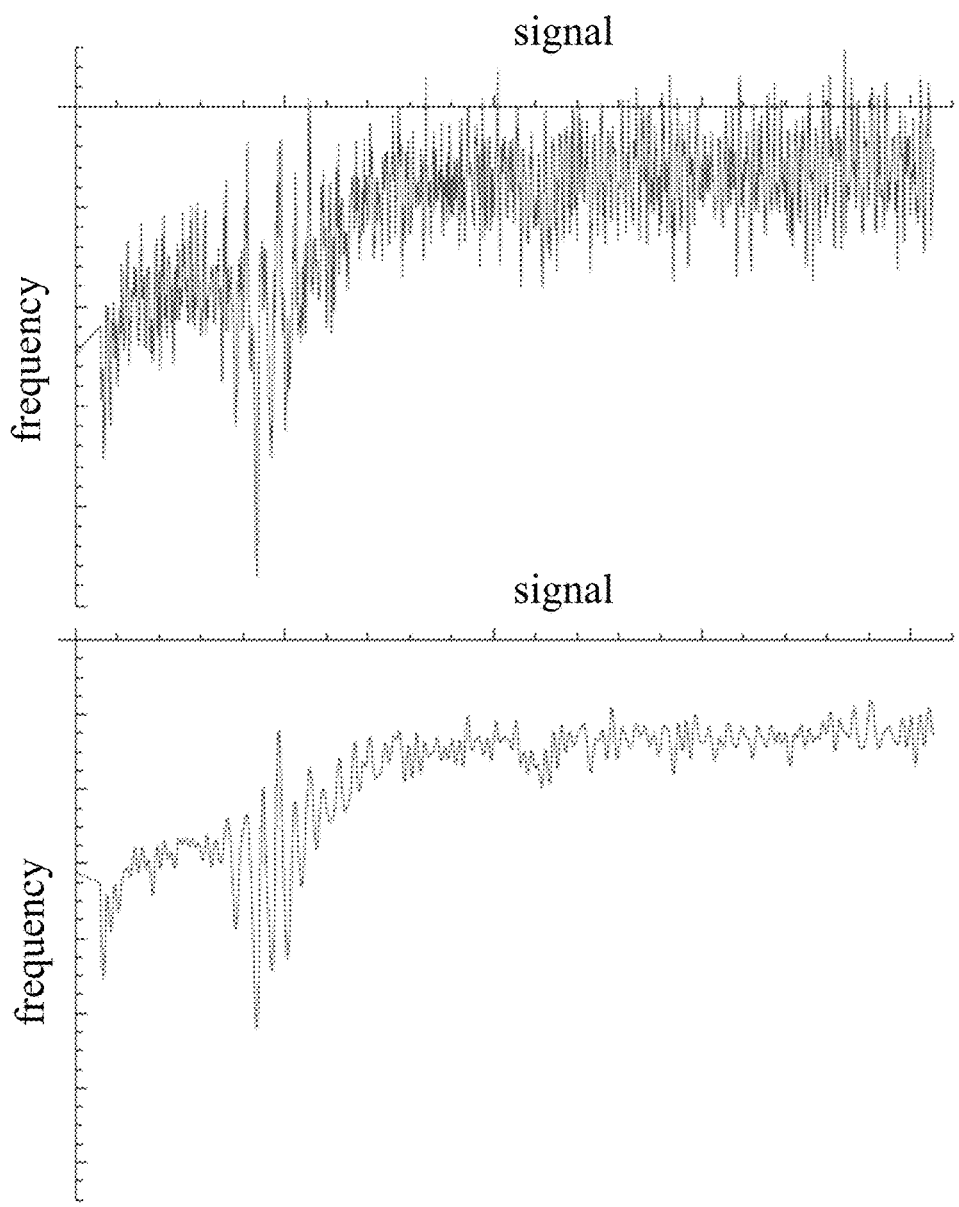
FIG. 7 illustrates a signal trace before and after noise removal in accordance with various embodiments.

In various embodiments, a method can comprise removing noise from a signal trace. Removing noise can comprise performing signal processing, such as to remove 60 Hz line noise. Removing noise from a signal trace can reduce the error of signal trace interpretation. An example of a signal trace produced by sequencing a 12-base nucleic acid template, before (upper signal trace) and after (lower signal trace) removal of 60 Hz line noise from the signal, is illustrated in FIG. 7. Various methods of noise removal may be used, depending on the character of such noise, and such methods are well known to a person of skill in the art in the field of signal processing.

In various embodiments, signal processing to determine the sequence of a target bound to a sensor may comprise a probabilistic determination of the identity of the target, rather than an exact determination of the sequence. The actual sequence of a target molecule may be one of a number of possible unique sequences, each possible unique sequence having a unique theoretical signal. A determination of the sequence of the target molecule may require a comparison of experimentally measured signal with a signal interpretation map comprising a database of unique theoretical signals. The signal interpretation map may be generated based on a training data set or library produced using known target sequences, signal processing based on positive and negative control measurements to reduce signal artifact such as noise, blur, drift, and the like, as well as application of machine learning and/or statistical methods such as neural networks, clustering, curve fitting, model fitting, Bayesian inference, etc.

Manufacturing and Assembly of a Sensor Device

In various embodiments of the present disclosure, a method of producing a molecular biosensor device as described herein is provided. A method of producing a molecular biosensor device can comprise a combination of CMOS fabrication processes and molecular biology methods. CMOS fabrications processes can comprise high-resolution optical lithography methods that are well known in the art and are suitable for commercial scale production of integrated circuits, including devices such as FETs. In various embodiments, CMOS fabrication processes can be used to produce integrated circuits comprising individual sensors having a first electrode and a second electrode deposited on a semiconductor base, with the first electrode and the second electrode separated by a precisely defined sensor gap. In a preferred embodiment, a nano-electrode, gap and contact design would be chosen so as to be manufacturable entirely within CMOS processes. In particular, if specific simple geometries are chosen for these elements, they can be fabricated using the high resolution optical lithography methods, such as Extreme UV (EUV) and Deep UV (DUV) sources, combined with phase-shifting masks, multiple-patterning, and other techniques used to achieve highest resolution CMOS fabrication nodes, including current and future 16 nm nodes, 14 nm nodes, 10 nm nodes, 7 nm nodes and 5 nm nodes as embodied by specific fabrication facilities, such as those at major foundry companies, (e.g., TSMC or GlobalFoundries). Such processes have uniquely high resolution for making certain specific pattern features, such as straight line segments, straight line cuts, and circular spots. Use of these process-specific geometric elements in the design of nano-electrode, nano-contact, and/or gap geometries can facilitate fabrication of a sensor device in accordance with various embodiments in the associated CMOS process. However, in general the manufacturing techniques employed may also comprise non-CMOS process methods, such as e-beam lithography, nano-imprint lithography, or milling and etching techniques such as focused ion beam milling and plasma etching. Molecular biology fabrication methods can comprise synthesis of the desired bridge molecules with precise control over the atomic configuration, and delivery of solutions of such biomolecules in a liquid phase under conditions suitable to permit interaction and coupling of the biomolecules with electronic sensor components produced in upstream CMOS or other fabrication method process, and/or with other biomolecules, in specifically designed self-assembly reaction processes.

In various embodiments, a method of manufacturing a sensor device described herein can comprise steps that including: manufacturing an integrated circuit microchip, fabrication of sensor electrodes and/or contacts, synthesis of a bridge biomolecule, assembling the bridge biomolecule to the electrodes and/or contacts, coupling a probe to the bridge biomolecule, and enclosing the sensor device in a flow cell. In various embodiments, a sensor can comprise a two terminal circuit, or a sensor can comprise a three terminal circuit with a gate. In various embodiments, a gate may have a buried gate configuration; however, lateral gate and other gate configurations, including finFET structures, may also be used.

In various embodiments, an electrode, contact, and/or gate may be comprised of conductive metal materials. For example, an electrode, contact, and/or gate may comprise aluminum, titanium, chromium, copper, gold, palladium, platinum, and the like. In various embodiments, an electrode, contact, and/or gate may comprise semiconductor materials, including doped semiconductor materials that may be used to produce n-type and p-type semiconductor electrodes. In various embodiments, an electrode and a contact attached to the electrode can comprise the same material, and in various other embodiments, a contact can comprise a material that is different from an electrode to which it is attached.

In various embodiments, an electrode may have any suitable structural configuration. For example, an electrode can comprise a generally rectangular cross-section, although other geometric and irregular cross-sectional profiles are possible and within the scope of the present disclosure. In various embodiments, an electrode can have a maximum cross-sectional dimension (i.e., the maximum dimension of the electrode in a cross-section of the electrode) of less than about 30 nm, or less than about 25 nm, or less than about 20 nm, or less than about 15 nm, or less than about 14 nm, or less than about 13 nm, or less than about 12 nm, or less than about 11 nm, or less than about 10 nm, or less than about 9 nm, or less than about 8 nm, or less than about 7 nm, or less than about 6 nm, or less than about 5 nm, or less than about 4 nm, or less than about 3 nm.

Similarly, in various embodiments, a contact may have any suitable structural configuration. For example, a contact can comprise a generally semi-spherical or hemi-spherical cross-sectional profile, although other geometric and irregular cross-sectional profiles are possible and within the scope of the present disclosure. In various embodiments, a contact can have a maximum cross-sectional dimension (i.e., the maximum dimension of the contact in a cross-section of the contact) of less than about 20 nm, or less than about 15 nm, or less than about 14 nm, or less than about 13 nm, or less than about 12 nm, or less than about 11 nm, or less than about 10 nm, or less than about 9 nm, or less than about 8 nm, or less than about 7 nm, or less than about 6 nm, or less than about 5 nm, or less than about 4 nm, or less than about 3 nm.

In various embodiments, the first electrode and the second electrode may be alternately referred to as a source and/or drain, and in various embodiments, a source and/or drain can comprise a distinct structural component from an electrode.

A method of manufacturing can comprise using lithography methods to define a first electrode location and a second electrode location on the surface of a substrate. The first electrode location and the second electrode location may be defined to produce a precisely defined electrode gap between them upon completion of electrode fabrication. Similarly, in various embodiments, a method of manufacturing can comprise using lithography methods to define a first contact position and a second contact position. The first contact position and the second contact position may be defined to produce a precisely defined contact gap between them upon completion of contact fabrication. Likewise, a contact can be configured with a defined structure. Various methods that may be used to manufacture a biosensor are described in greater detail below.

Figure 8:
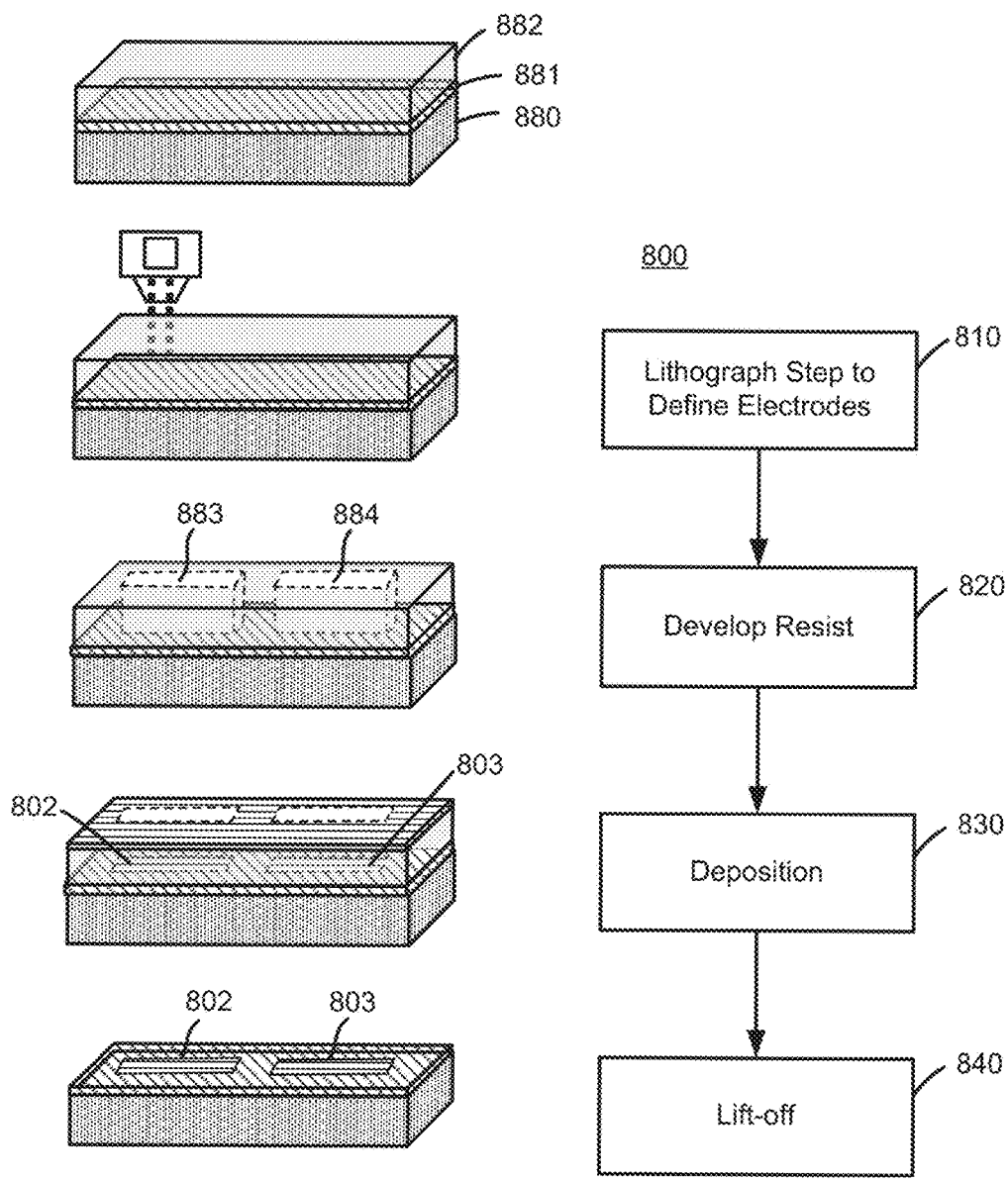
FIG. 8 illustrates a process flow for a method of fabricating electrodes using CMOS techniques in accordance with various embodiments.

With reference now to FIG. 8, a lithographic method 800 for fabricating electrodes is illustrated. In various embodiments, a fabrication method may begin with a microchip substrate such as a silicon substrate 880 overlayed with a silicon oxide layer 881 a resist layer 882. The resist layer can comprise any suitable resist material suitable, such as poly (methyl methacrylate). Adhesion promoters may also be used in a fabrication process in accordance with the present disclosure. In the illustrated embodiment, e-beam lithography is used to expose the resist layer and to define a first electrode track 883 and a second electrode track 884 in the resist layer (step 810). Following the lithography step, the resist is developed (step 820) to remove the resist in the areas defined in the lithography step. Next, a deposition step (step 830) may be performed to form a first electrode 802 and a second electrode 803 on the substrate surface. Any suitable material and deposition method may be used, including, for example, metal sputter coating. Likewise, any suitable substrate surface treatment, such as application of an intermediate attachment layer to provide suitable bonding between electrode and substrate, may be performed prior to performing the deposition step. In various embodiments, the first and second electrodes are fabricated from gold using a sputtering deposition method. Following the deposition step, a lift-off step (step 840) is performed to remove the remaining resist, leaving the first electrode and the second electrode disposed on the surface of the substrate.

In various embodiments, a lithographic method for fabricating nano-electrodes such as method 800 can achieve highly precise electrode configurations. For example, the electrodes can be configured with consistent length, width, and thickness specifications. In various embodiments, an electrode can have a width of between about 10 nm and about 40 nm, such as a width of about 20 nm. Likewise, the electrode gap defined by the first electrode and the second electrode can be configured with a precise electrode gap dimension. In various embodiments, the electrode gap dimension may be between about 3 nm and about 30 nm. For example, the electrode gap for a pair of electrodes in a sensor in accordance with various embodiments can be between about 3 nm and about 30 nm, or between about 4 nm and about 25 nm, or between about 5 nm and about 20 nm, or between about 6 nm and about 17 nm, or between about 7 nm and about 15 nm. In various embodiments, an electrode gap can be fabricated with a dimension of about 3 nm, about 4 nm, about 5 nm, about 6 nm, about 7 nm, about 8 nm, about 9 nm, about 10 nm, about 11 nm, about 12 nm, about 13 nm, about 14 nm, or about 15 nm. As will be evident to a person of ordinary skill in the art, the various method steps described above can be used to produce multiple pairs of electrodes in parallel at high density and with highly precise physical specifications in a process amenable to commercial-scale production of sensor devices using CMOS fabrication and/or other microelectronic fabrication methods.

Without wishing to be bound by theory, providing a sensor having an electrode gap (or a sensor gap) with an electrode gap dimension as described above may provide various advantages with respect to sensor performance and/or fabrication. For example, for an electrode gap having a dimension below about 3 nm, spurious sources of current conduction through the solution (i.e., the sample environment) and bulk will start to increase, creating added noise. In addition, such gaps may not be large enough to accommodate various probe molecules of interest, such as enzymes. Moreover, such gaps are not compatible with current CMOS manufacturing capabilities. The cost and complexity of manufacturing bridge molecules with atomically precise specifications for electrode gaps greater than about 30 nm, such as by using biopolymers or chemically synthesized molecules, rises substantially, and the rigidity various bridge molecules may decrease with lengths beyond about 30 nm. Likewise, the conductivity of many molecules drops substantially below useful parameters beyond those lengths, and greater lengths also limit the ability to closely pack sensors in high density arrays. Thus, sensors with electrode gaps in the range of about 3 nm to 30 nm may afford certain advantages with respect to the function, manufacturability, scalability and economics of a sensor device.

Figure 11A:
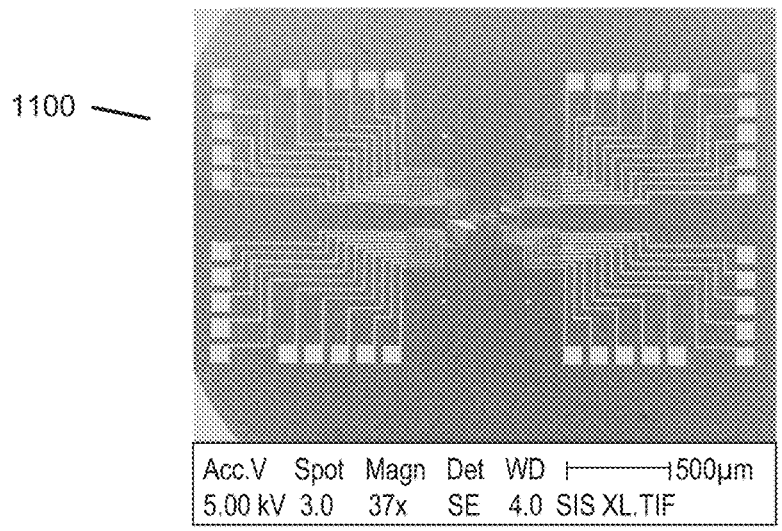
FIGS. 11A-11C illustrate views of a sensor device fabricated using CMOS techniques in accordance with various embodiments.
Figure 11B:
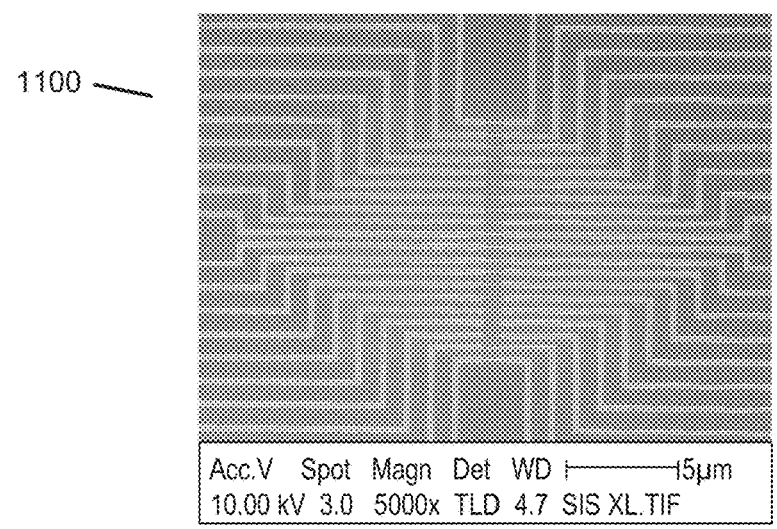
Figure 11C:
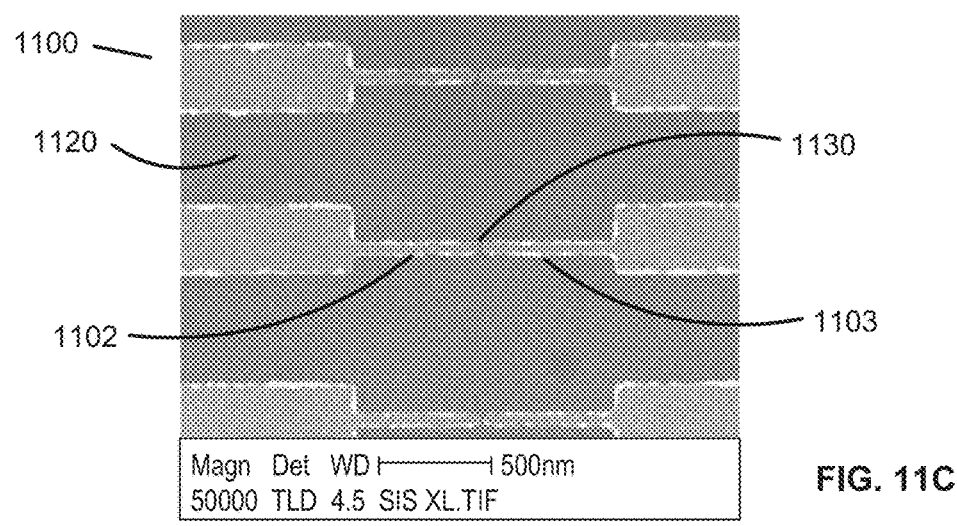

An example of a sensor device fabricated in accordance with the method described above is illustrated in FIGS. 11A-11C, which shows scanning electron micrographs of the surface of a sensor device 1000 at 37-fold, 5000-fold, and 50,000-fold magnification, respectively. Sensor device 1000 comprises nano-electrodes and nano-contacts for 20 sensors, as well as leads and pads for connection to an external current meter. Pads and leads located on the surface of the substrate are clearly visible in FIG. 11A. Sensor electrodes appear as a lighter vertical band in the center of FIG. 11B. In FIG. 11C, first electrodes 1102 and second electrodes 1103 can be seen clearly, along with electrode gap 1120 defined between the first and second electrodes.

Figure 9:
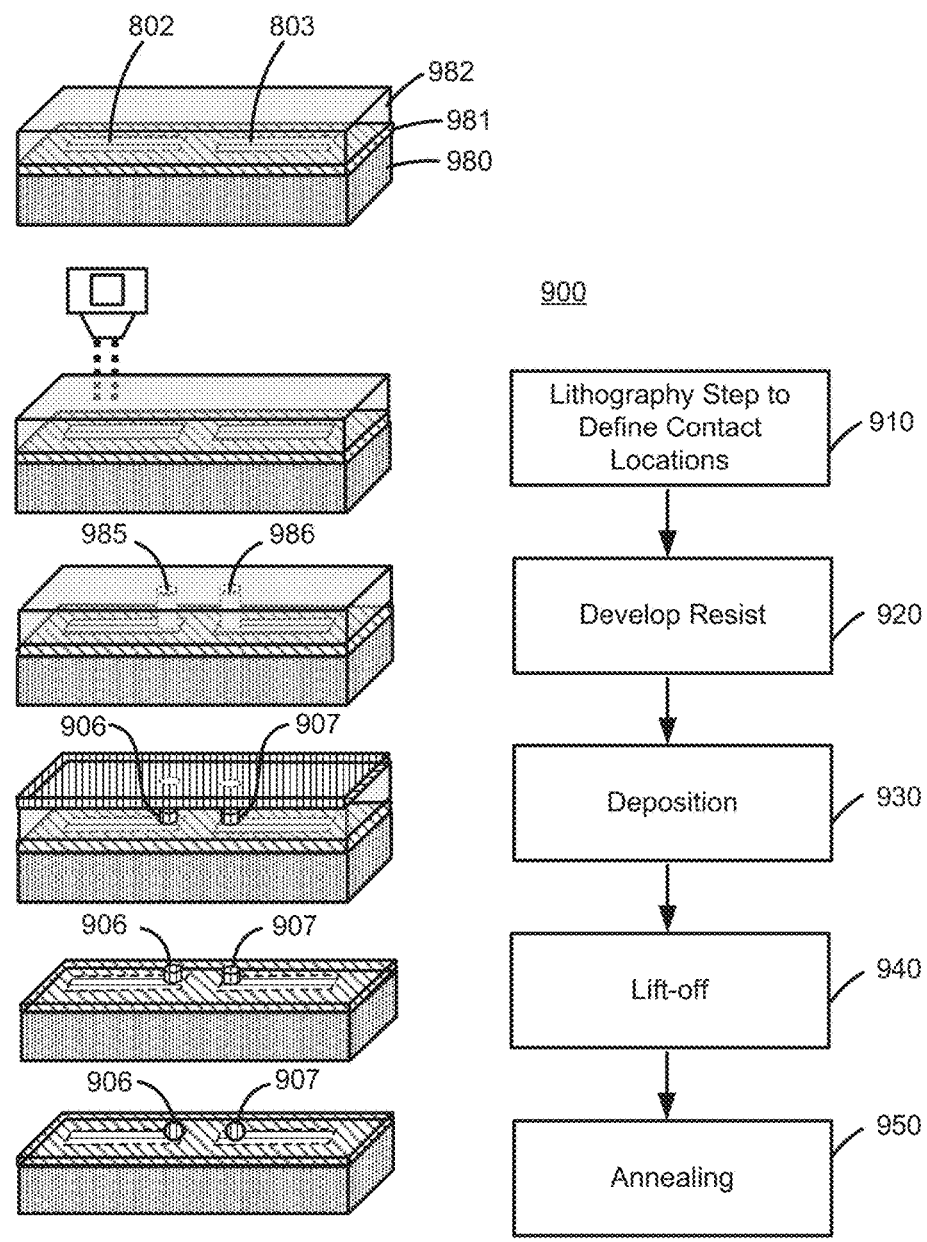
FIG. 9 illustrates a process flow for a method of fabricating contacts using CMOS techniques in accordance with various embodiments.

In various embodiments and with reference now to FIG. 9, a method of manufacturing a biomolecular sensing device can comprise a lithographic method 900 for fabricating and/or determining the location of a contact. In various embodiments, a fabrication method may begin with a microchip comprising a substrate on which a first electrode 802 and a second electrode 803 are disposed. The microchip can comprise silicon substrate 880 overlayed with silicon oxide layer 881 and a suitable resist layer 982. In the illustrated embodiment, e-beam lithography is used to expose the resist layer and to define a first contact position 985 and a second contact position 986 in the resist layer (step 910). In various embodiments, the location of the contact may be defined to overlay one of the first electrode and the second electrode, such as near a distal end of the electrode adjacent to the electrode gap. The size and pattern defined for the contact may contribute to determining the size and shape of the contact formed in later process steps, as described below. Following the lithography step, the resist is developed (step 920) to remove the resist in the contact positions defined in the lithography step. Next, a deposition step (step 930) may be performed to form a first contact 906 and a second contact 907 on the first and second electrode surfaces. As for the electrodes, any suitable material and deposition method may be used. Likewise, any suitable substrate surface treatment, such as application of an intermediate attachment layer to provide suitable bonding between electrode and substrate, may be performed prior to performing the deposition step. The contacts can comprise a different material from the electrodes, or the contacts can comprise the same material used to fabricate the electrodes. In various embodiments, the first and second contacts are fabricated from gold using an electrochemical deposition method. Following the deposition step, a lift-off step (step 940) is performed to remove the remaining resist, leaving the first contact and the second contact disposed on the surfaces of the first and second electrodes.

Alternately, in various embodiments, a method for fabricating a contact can comprise deposition of preformed contact nanoparticles. Preformed contact nanoparticles can be deposited into a void formed in a resist layer and configured to receive a contact nanoparticle and position it at a contact position, or contact nanoparticles can be deposited using a chemical derivatization layer to achieve attachment at a contact position.

Figure 10:
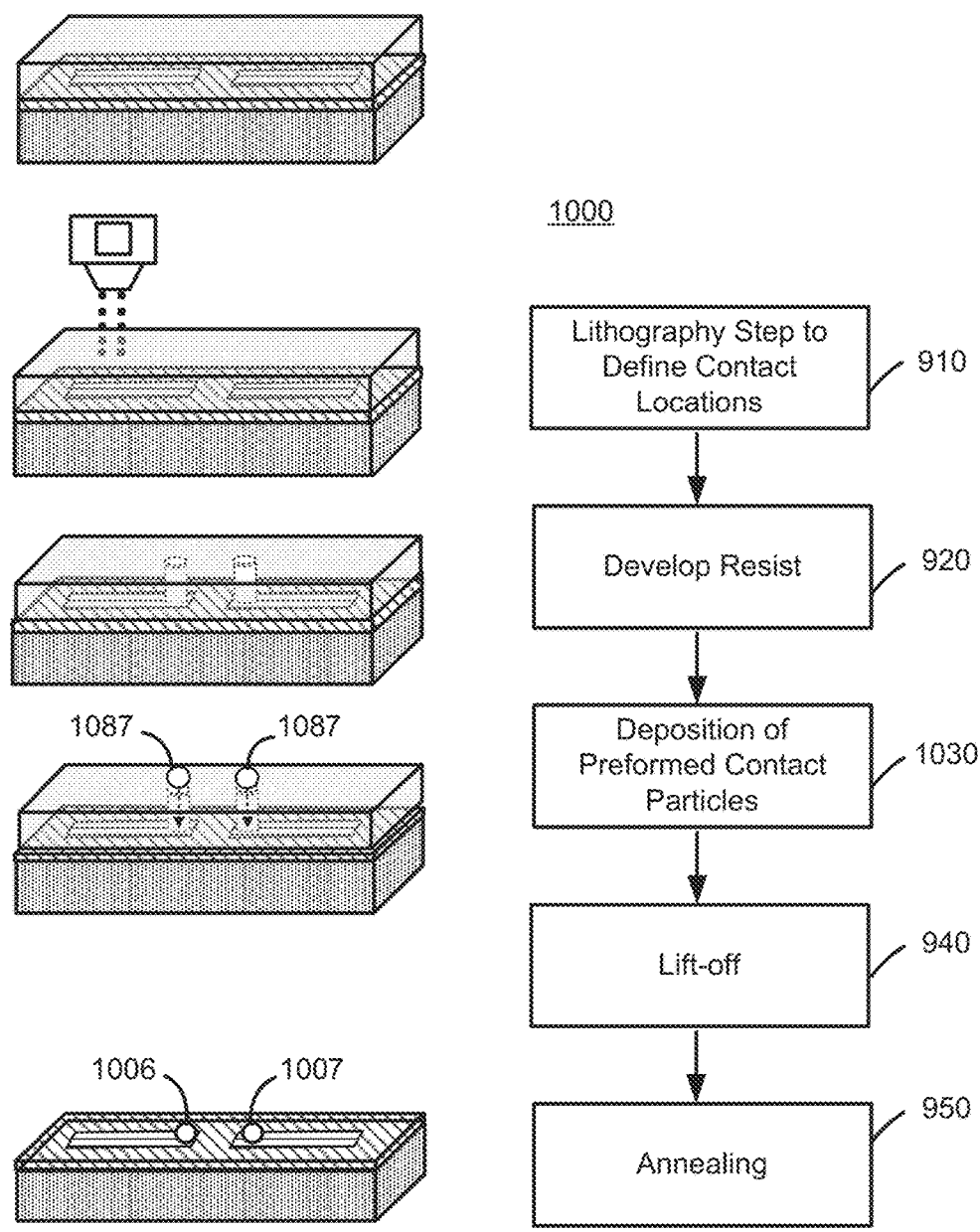
FIG. 10 illustrates a process flow for a method of fabricating contacts using CMOS techniques and deposition of preformed contact particles in accordance with various embodiments.

As illustrated in FIG. 10, a method 1000 of depositing a preformed contact particle into void formed in a resist layer can comprise the same steps described above for method 900 with respect to steps 910 and 920. Following creation of a void configured to receive a preformed contact particle, a solution comprising a plurality of preformed contact particles 1087 can be contacted with the device (step 1030) and the particles deposited into the voids using pressure, mixing, surface tension, buoyancy, centrifugal force, or other methods to introduce a particle into a void. Following deposition of the particles, excess solution and particles may be removed. A lift-off step can be performed to remove remaining resist as described above with respect to step 940, and the preformed contact particles can optionally be annealed to the electrodes in a subsequent as necessary to form strongly attached first and second contacts (1006, 1007).

Alternately, a method of depositing preformed contact nanoparticles using a chemical derivatization treatment can comprise steps similar to steps 910 and 920 described above with respect to the method illustrated in FIG. 9. For example, one such widely used surface derivatization compatible with a silicon substrate surface is silanization, which can include coating a substrate surface with molecules such as aminosilanes (for example, APTES) or mercaptosilanes (for example, MPTES). These molecules adhere to a silicon surface, and then their exposed ends readily cross-link to other materials such as gold nanoparticles to bind them to the surface. Then, in a step similar to step 930, such a derivatization treatment can be applied rather than depositing a contact metal or other material. After a lift-off step similar to step 940 is performed, the first electrode and the second electrode will comprise a surface derivatization at the locations intended for attachment of the first contact and the second contact. The device comprising the derivatized electrode surfaces can be contacted with a solution comprising a plurality of preformed contact particles. The particles may have a surface or coating that is complimentary to or otherwise binds specifically to the derivatized electrode surfaces, thereby localizing the contact particles to the defined contact positions. The derivatization treatment and any particle coating may be removed in a removal step, as necessary, and the preformed contact particles annealed to the electrodes as described above. An example of this approach is the use of an APTES-coated silicon surface to specifically bind a gold nanoparticle.

In various embodiments, contact structures can be created by various direct means, such as positioning gold nanoparticle beads on electrodes by use of atomic force microscopy (AFM), or by deposition of excess beads followed by AFM removal of unwanted beads.

In various other embodiments, contact structures and/or an electrode gap can be formed in place via material removal, such as by using focused ion beam (FIB) milling. For example, an electrode gap can be carved into a previously established continuous metal nanowire using FIB, thereby creating a first electrode and a second electrode simultaneously with forming the electrode gap.

Following fabrication of the electrodes and contacts of a sensor or array of sensors, the sensor(s) may be enclosed in a flow cell or similar device suitable to permit controlled introduction of a liquid solution to the sensor(s). Enclosing the sensor chip in a flow cell is typically done by molding a flow cell from PDMS or other polymer or plastic, and using this to encase the chip, leaving the fabricated electrodes and contacts suitably exposed for bridge and probe assembly as well as subsequent assays using the completed sensor(s). In various embodiments, a surface passivation treatment may be applied to the substrate surface and portions of the exposed electrodes to reduce electrical noise that can occur from contact with liquid samples. The passivation treatment can be applied to leave the electrodes and/or contacts in the area of the sensor gap untreated. For example in various embodiments, a 30 nm wide area aligned with the sensor gap may be left untreated. The passivation treatment may be performed prior to enclosing the sensor chip with a flow cell. A sensor in accordance with various embodiments can have electronic noise of less than about 1 pA, or less than about 0.9 pA, or less than about 0.8 pA, or less than about 0.7 pA, or less than about 0.6 pA, or less than about 0.5 pA, or less than about 0.4 pA, or less than about 0.3 pA, or less than about 0.2 pA, when a voltage of about 0.5 V is applied and the sensor is immersed in a low ionic strength buffer solution otherwise suitable to support activity of an enzyme, for example DNA polymerase I enzyme.

Fabrication of a biopolymer bridge can be performed by any of a variety of methods that may be used to synthesize biopolymer molecules, including in vivo synthesis methods, in vitro enzymatic synthesis methods, chemical synthesis methods, or any combination thereof. Various methods for producing biopolymer molecules suitable for use as a bridge molecule in accordance with the present disclosure will be well known to a person of ordinary skill in the art. Likewise, methods for derivatizing or modifying a biopolymer bridge molecule to provide an anchor or a linker component as described herein are likewise well known. The various specific biopolymer bridge molecules described herein are provided by way of example and should not be interpreted as limiting the scope of the present disclosure, and synthetic bridge molecules may be used in accordance with various embodiments of the present disclosure.

In various embodiments, attachment of a biopolymer bridge molecule to a probe may be performed by a self-assembly chemical reaction. Likewise, attachment of a biopolymer bridge molecule to electrodes or contacts may also be performed by a self-assembly chemical reaction. Such self-assembly reactions may be performed by putting the two components to be attached into contact with one another via a solution comprising at least one of the components. In various embodiments, attachment of a biopolymer bridge to a probe can be performed before, after, or simultaneously with attachment of the bridge to electrodes or contacts. Similar considerations apply to a bridge molecule produced by synthetic chemistry.

In various embodiments, a method of making a sensor device includes assembling a biopolymer bridge molecule to the first electrode and the second electrode. The bridge molecule assembly step can comprise a self-assembly step. Self-assembly can be performed by contacting the partially constructed sensor device comprising the first and second electrode with a solution comprising the bridge molecule. The bridge molecule can self-assemble to the first electrode and the second electrode based on an affinity between the first end and the second end of the bridge molecule and the first electrode and the second electrode. In various embodiments, self-assembly of the sensor components can be monitored electronically by the sensor device, as described below in Example 2 and with reference to FIGS. 13-15. Electronic monitoring can provide a quality control function and serve to identify sensors in a device that are properly assembled. Signal from sensors circuits that do not provide assembly process signals within predetermined parameters may be disregarded in downstream analyses, such as sequencing analyses, performed with the device.

Example 1

Biopolymer Bridge Self-Assembly

Figure 12:
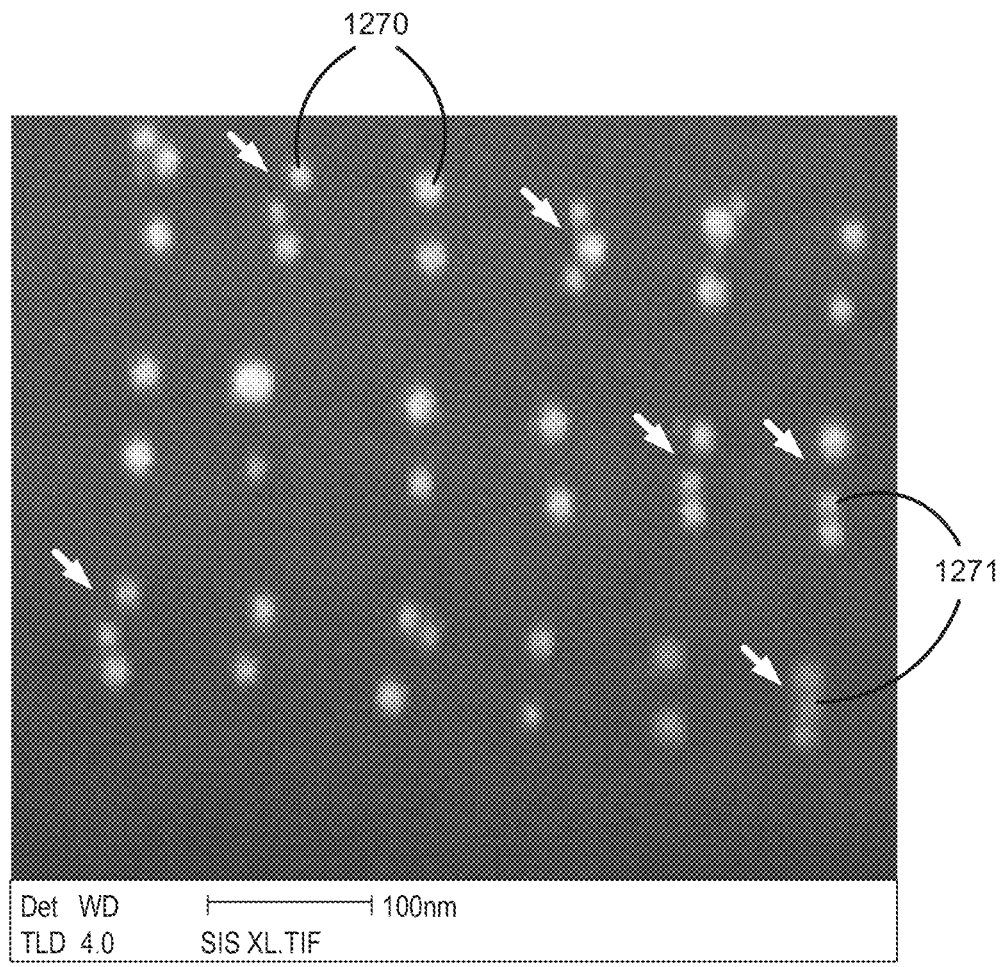
FIG. 12 illustrates a scanning electron micrograph of a contact array following biopolymer bridge self-assembly in accordance with various embodiments.

A double-stranded DNA biopolymer bridge molecule with an end-to-end length of about 20 nm was constructed using the oligo set forth in SEQ ID NO: 1 comprising a 5'-thiol modification and the oligo set forth in SEQ ID NO.: 2 comprising a 5'-thiol modification and an internal biotin modification. The bridge molecules were labelled for visualization purposes using a streptavidin-gold tag. A test array 1200 (FIG. 12) of gold nanoparticle contacts was fabricated using e-beam lithography techniques to deposit pairs of gold contacts, each pair of contacts defining a contact gap of about 20 nm, center-to-center. A buffered solution comprising the gold-labelled bridge molecules was placed in contact with the test array of gold nanoparticle contacts. Following a brief incubation period, excess solution was removed and the array was washed and imaged by scanning electron microscopy (SEM). An SEM image showing the arrangement of gold contacts 1270 and gold tags 1271 is illustrated in FIG. 12. For several contact pairs (indicated with arrows), a gold tag 1271 can be seen disposed between the contact pair, indicating successful self-assembly of the biomolecular bridge molecule to the pair of contacts.

Example 2

Detection of Self-Assembly Steps

Figure 14:
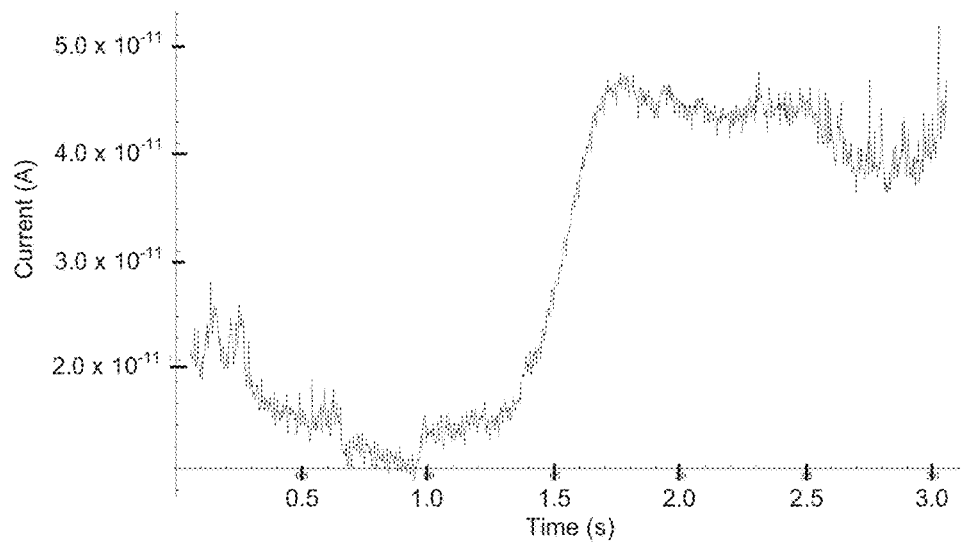
FIG. 14 illustrates a signal trace produced during a process of probe binding to a biopolymer bridge of a sensor in accordance with various embodiments.
Figure 15:
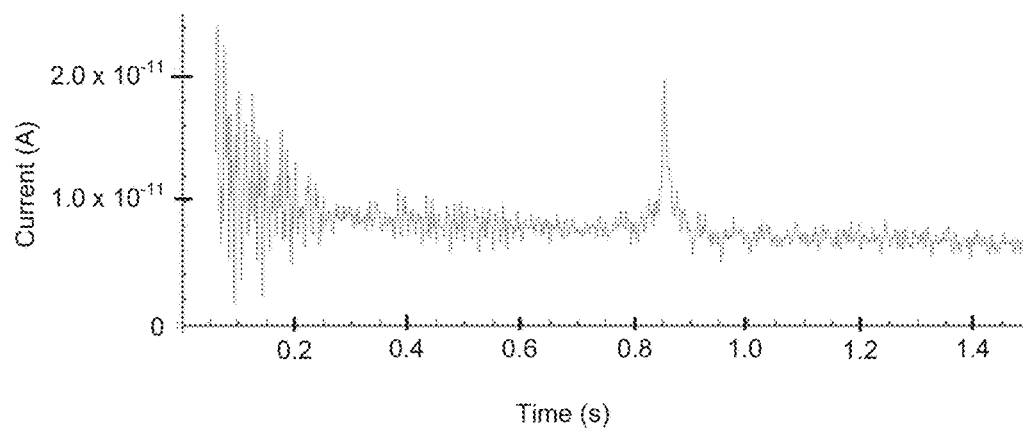
FIG. 15 illustrates a signal trace produced during template binding to a probe in accordance with various embodiments.
Figure 16:
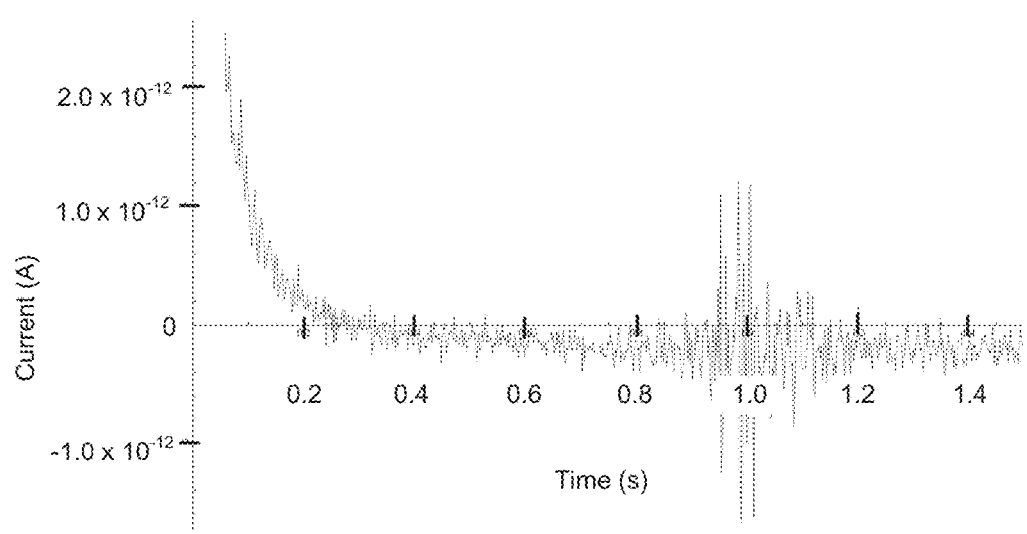
FIG. 16 illustrates a signal trace produce during template-dependent base incorporation by a probe in accordance with various embodiments.

A sensor device with a single sensor comprising gold contacts attached to electrodes with a contact gap of about 20 nm, center-to-center, was fabricated using e-beam lithography techniques. The sensor was enclosed with a PDMS flow cell comprising a 1 mm wide by 0.4 mm high channel that was open on either end to permit introduction of liquid into a first end of the flow cell interior and displacement of liquid from the second end of the flow cell, and solution the cell contacting the sensor. The flow cell channel was oriented orthogonally to the direction of the electrodes comprising the sensor, with the sensor located in approximately the middle of the length of the flow cell channel. A low ionic strength buffer solution was introduced into the flow cell, and a 0.5 V potential was applied to the sensor throughout subsequent serial steps of introduction and self-assembly of a double-stranded DNA bridge molecule (as described above for Example 1, but without a gold tag) (FIG. 13), introduction and binding of a streptavidin-tagged Klenow fragment (FIG. 14), introduction and binding of a 50 base primed single-stranded DNA molecule (FIG. 15), and introduction of a dNTP mix to initiate template-based synthesis by the Klenow fragment (FIG. 16). The sequence of the DNA template molecule include the following oligo sequence featuring a poly-A region:

```
                                        (SEQ ID NO: 14)
  5'-cgc cgc gga gcc aag aaa aaa aaa aaa aaa aaa aa ttgcatgtcctgtga-3'
``` and the primer used was:

```
  3'-aac gta cag gac act-5'    (SEQ ID NO: 15)
```

In addition, similar sequences with the poly-A tract replaced by poly-C, G, and T tracts were used to investigate the effect of different template bases.

Figure 13:
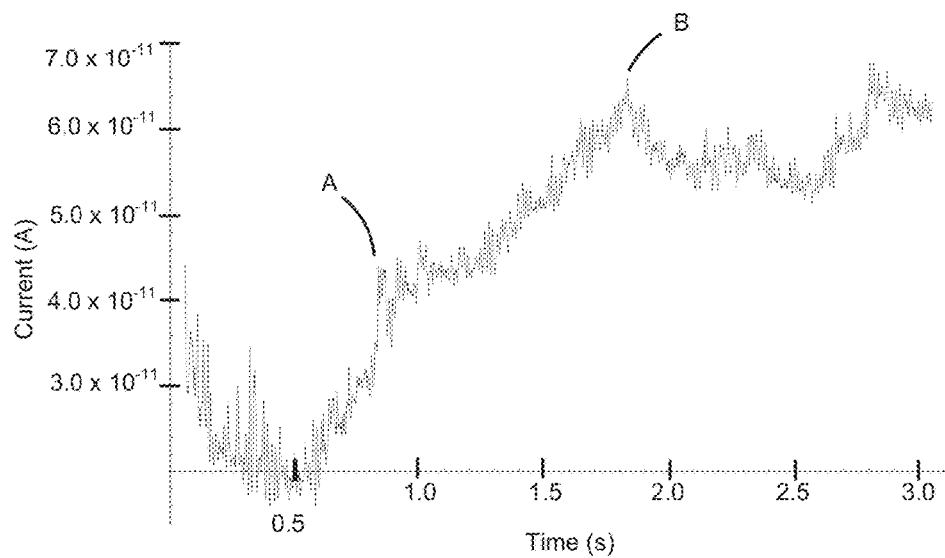
FIG. 13 illustrates a signal trace produced during a biopolymer bridge self-assembly event for a sensor in accordance with various embodiments.

As illustrated in FIG. 13, the measured current rises over a three second period. The two inflections points (A and B) in the signal trace are thought to correspond to binding of the 5'-thiol-modified terminal base anchors to the first and second contact. The signal trace following introduction of a solution comprising streptavidin-tagged Klenow fragment (FIG. 14) exhibits a sharp increase in current at about 1.5 s that is likely to correspond to a streptavidin linker component of a Klenow fragment enzyme contacting and binding the biotin linker component of the biopolymer bridge. In FIG. 15, a sharp signal peak is present in the signal trace following introduction of the template strand to the flow cell, with the peak interpreted to correspond to template binding by the Klenow fragment. The signal trace measured following introduction of a dNTP mix comprising all for DNA bases, illustrated in FIG. 16, likewise exhibits a distinct signal feature at about 1 s. This may represent dissociation of the synthesized duplex from the polymerase enzyme, and the signal trace from about 0.7 s to about 0.95 s may correspond to the kinetic signature produced by the sensor in response to nucleotide incorporation based on the bound template DNA.

Example 3

Detection of Nucleotide Base Incorporations

Figure 17:
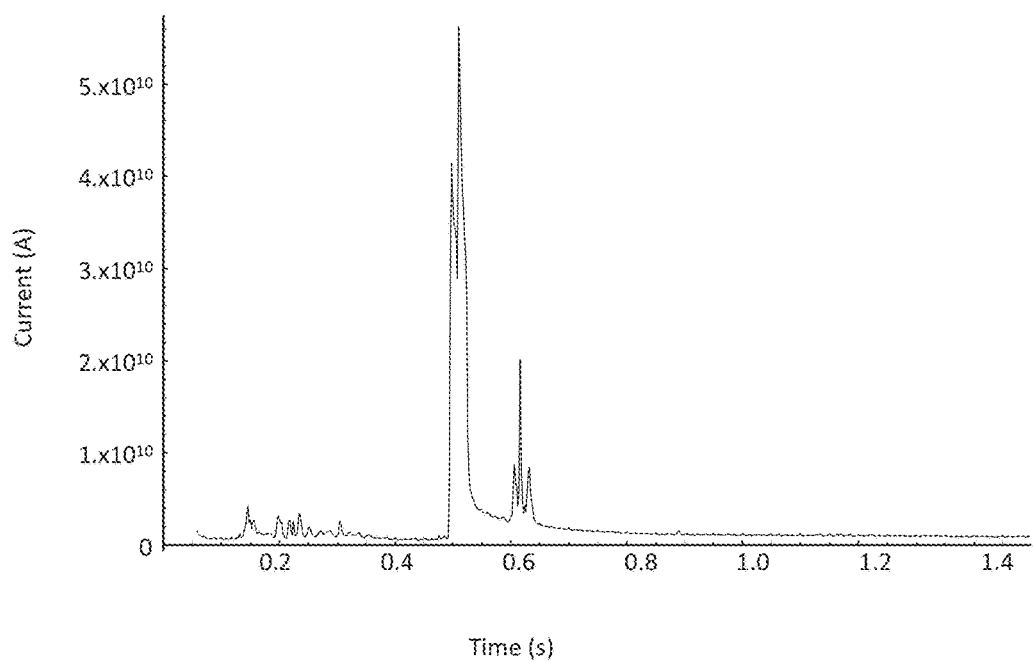
FIG. 17 illustrates a signal trace produced by a single template-dependent base incorporation event by a sensor in accordance with various embodiments.
Figure 18:
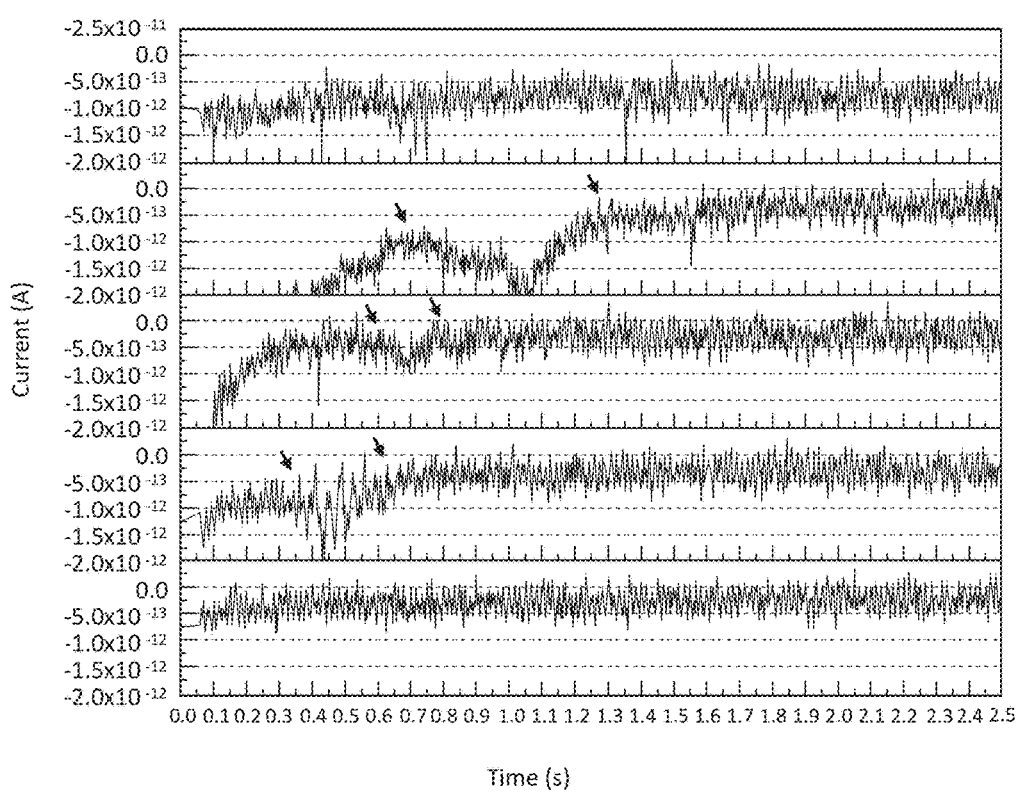
FIG. 18 illustrates signal traces produced by a sensor in accordance with various embodiments under various experimental conditions.

A sensor device comprising a biopolymer bridge molecule and Klenow fragment probe was fabricated and assembled as described above in Example 2. The sensor device was used to produce signal traces in response to DNA synthesis reactions performed using single-stranded DNA templates of various lengths and sequence compositions. FIG. 17 illustrates a signal trace for a template sequence that provides for the incorporation of a single base. The signal feature at 0.5 s is interpreted to correspond to the template-dependent activity of the Klenow fragment and base incorporation, and the much weaker signal features just after 0.6 s are interpreted to correspond to some form of noise or spurious signal in the system. FIG. 18 illustrates signal traces for various template tracts. The template and primer described above in Example 2 were used for the illustrated reactions.

The top and bottom signal traces are control experiments in which buffer without dNTPs is introduced to a sensor. The second, third, and fourth signal traces (from top to bottom) were produced in response to introducing dTTP into solution (expected to result in 20 incorporation events directed by the 20 A bases of the template), followed by addition of dCTP (expected to allow another 3 incorporations directed by the GAA triplet in the template, 3' to 5'), followed by the addition of dNTP (expected to polymerize as directed remaining 12 bases of the template) so that the signals produced result from 20, 3, and 12 incorporation events. The signal trace comprising the signal features located between arrows for each signal trace is interpreted to correspond to signal modulation due to template-dependent enzyme activity. The relative durations of these perturbed signal regions is in the expected proportion of 20:3:12, and the third such tract displays a clear spike that may correspond to the 12 discrete incorporation events. FIG. 7 illustrates an additional example of a signal trace produced by a DNA synthesis reaction performed using the device described above and the template described above with 12 unpaired template bases. These results demonstrate that a sensor in accordance with various embodiments can produce a signal trace comprising signal features in response to template-dependent DNA polymerase probe activity. This also demonstrates the value of noise removal in clarifying the signal: the upper panel in FIG. 7 is the raw measured signal, and the lower panel has undergone signal processing to remove noise, in this case specific 60 Hz line noise was eliminated with a bandpass filter.

Example 4

Detection of Methylated Template Bases

A sensor device comprising a biopolymer bridge molecule and Klenow fragment probe was fabricated and assembled as described above in Example 2. The sensor device was used to produce signal traces in response to DNA synthesis performed using a single-stranded DNA template comprising both cytosine and 5-methylcytosine modified nucleotides. The template sequence included unpaired base nucleotides having the sequence 5'-13x(N)-5x(GmC)-5x(GC)-G-3' (i.e., 5'-NNN NN NN NN NGmC GmCG mCGmC GmCG CGC GCG CGC G-3' (SEQ ID NO: 12), where N is any standard nucleotide and where mC is 5-methylcytosine). This template sequence was designed to produce a complementary synthesized strand having the sequence 5'-C-5x(GC)-5x(G̲C)-13x(N)-3' (i.e., 5'-CGC GCG CGC GCG̲ C G̲C G̲CG̲ CGC NNN NNN NNN NNN N-3' (SEQ ID NO: 13)), with the underlined guanosine bases corresponding to the positions of the 5-methylcytosine modified nucleotides in the template strand. A 0.5 V was applied to the sensor, and current was measured through the course of sequential introductions and incubations with water, buffer, a buffered solution of dCTP, a buffered solution of dGTP, and a buffered solution with a mix of all four dNTP bases. The expected result of this would be a single dCTP incorporation event, then 20 dGTP and dCTP incorporation events, the first 10 of which are against the unmodified cytosine bases, and the latter 10 against the 5-methylcytosine modified nucleotides. Detection of methylation would show up as a different character of signal in the second 10 of these 20 events.

Figure 19:
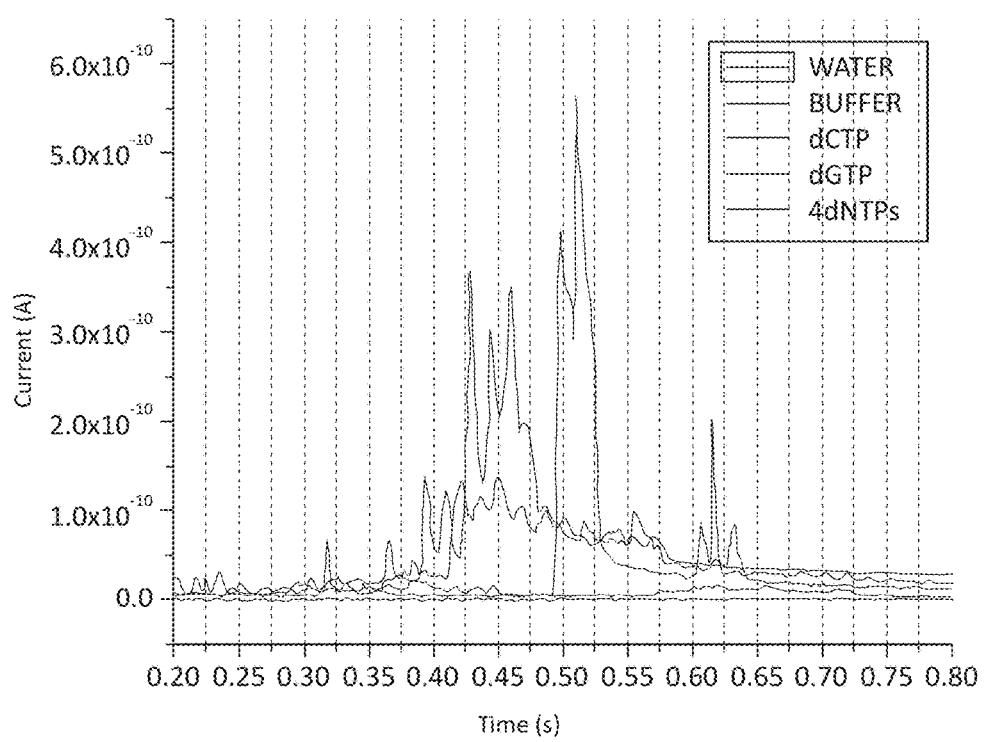
FIG. 19 illustrates a signal traces produced by a sensor in accordance with various embodiments under various conditions in response to a target comprising unmodified and 5-methylcytosine modified nucleotides.

Signal traces produced during incubation with each reagent are illustrated in FIG. 19. Incubation with water and buffer produced very low, baseline current with little variation. Addition of a solution comprising dCTP produced a sharp sequence feature corresponding to a single base incorporation of dCTP against the template lead base G. Addition of dGTP, creating a solution comprising both dCTP and dGTP, permitted synthesis through the 10 base incorporations corresponding to unmodified nucleotides followed by synthesis through the 10 base incorporations corresponding to the 5-methylcytosine bases in the template strand. The signal trace produced in this incubation period shows signal features with higher current from about 0.35 s to about 0.5 s, followed by signal features with lower current from about 0.5 s to about 0.65 s. This shift in signal amplitude is interpreted as a distinct change in the sensor signal in response to the effect of the methylation status of the template sequence on the polymerase and resultant signal modulation. This evidence supports the ability of a sensor in accordance with various embodiments of the present disclosure to directly distinguish the presence of modified nucleotides in a target sequence during a sequencing reaction.

Example 5

Detection of Signal Over Long DNA Strand Reads

A sensor device comprising a biopolymer bridge molecule and Klenow fragment probe was fabricated and assembled as described above in Example 2. The sensor device was used to produce signal traces in response to DNA synthesis performed using a single-stranded DNA template comprising an approximately 5400 bp template sequence derived from the genome of phi X 174 bacteriophage. A dNTP mix was provided in the experimental sequencing reaction, while a ddNTP (dideoxynucleotide triphosphate) mix was provided for a control reaction. The ddNTP mix terminates the polymerization process after one incorporation of such a dideoxy terminator, and thus essentially no sequencing sensing signal should result. The data was acquired at 20 ms time sampling resolution, which is too coarse to observe individual incorporation spikes, but allowed data collection for a timer period over 300 seconds, long enough to observe the entire polymerization process at the expected enzyme rate of approximately 20 bases per second.

Figure 20:
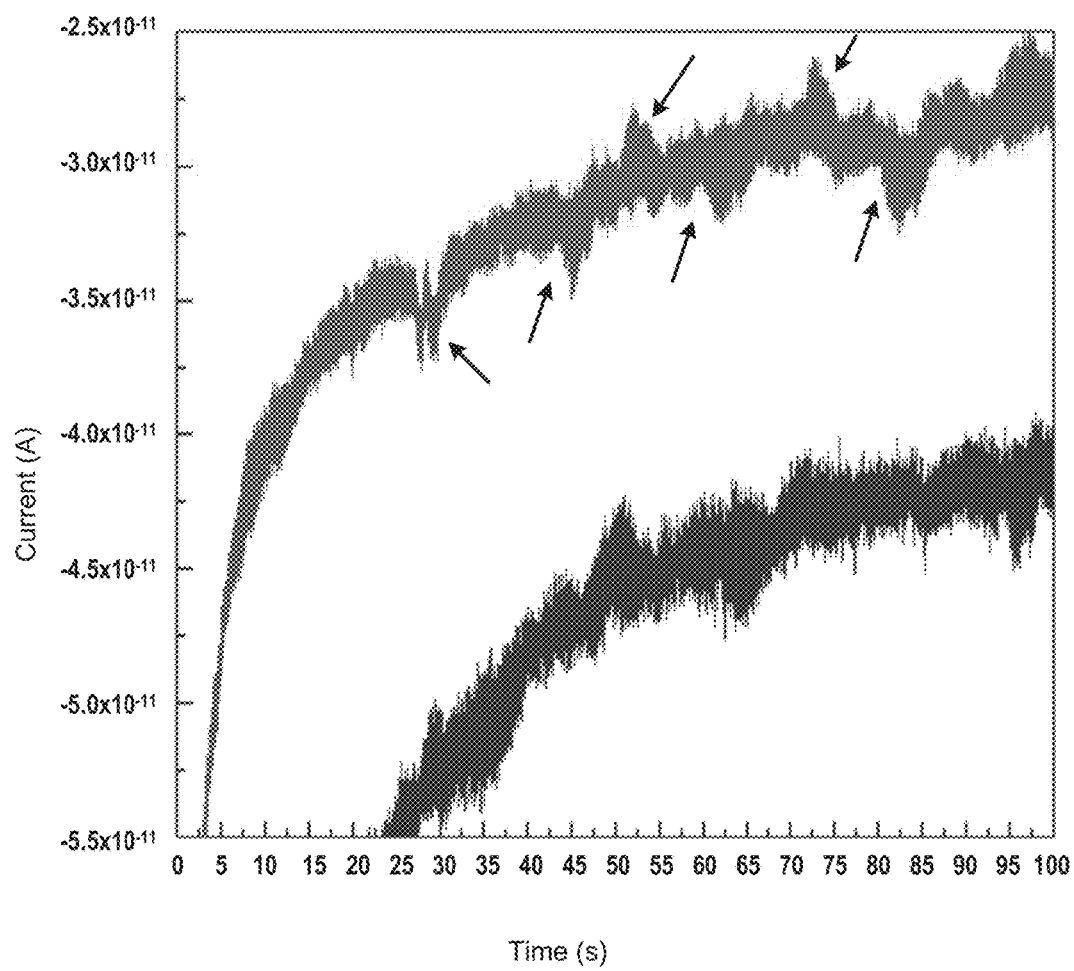
FIG. 20 illustrates signal traces produced by a sensor in accordance with various embodiments in response to a long template sequence under various experimental conditions.

FIG. 20 illustrates the signal trace produced by the experimental reaction with a dNTP mix (upper signal trace) compared to that for the control reaction using a ddNTP mix (lower trace). The signal trace for the experimental sequencing run included a number of distinct, gross signal features (noted with arrows) lacking in the control reaction and also produced a higher current than the control reaction. The signal trace produced over the 100 second period shown suggests that a sensor in accordance with various embodiments of the present disclosure may be suitable to produce a detectable signal in response to template-based nucleotide incorporation activity of a DNA polymerase probe over the course of an extended sequencing run for a long template sequence. Thus, there is no immediate limitation on the length or template such a sensor can process.

ADDITIONAL EXAMPLES

Additional nonlimiting examples of the disclosure include the following.
1. A sensor comprising:
a first contact coupled to a first electrode;
a second contact coupled to a second electrode;
a sensor gap defined between one of the first contact and the first electrode and one of the second contact and the second electrode; and
a bridge molecule comprising a first end and a second end;
wherein the bridge molecule is a biopolymer bridge molecule; and
wherein the bridge molecule is coupled to the first contact at the first end and coupled to the second contact at the second end.
2. A sensor comprising:
a first electrode overlying a substrate surface;
a second electrode overlying the substrate surface;
a sensor gap defined between the first electrode and the second electrode; and
a bridge molecule comprising a first end and a second end;
wherein the sensor gap comprises a sensor gap dimension of between about 5 nm and about 30 nm; and
wherein the bridge molecule is coupled to the first contact at the first end and coupled to the second contact at the second end.
3. The sensor as in examples 1 or 2, further comprising a gate electrode.
4. The sensor of example 1, wherein the sensor gap has a sensor gap dimension of between about 5 nm and about 30 nm.
5. The sensor as in examples 1 or 2, wherein the first end comprises a first self-assembling anchor and/or the second end comprises a second self-assembling anchor.
6. The sensor of example 2, wherein the bridge molecule comprises a biopolymer bridge molecule.
7. The sensor of any of examples 1-6, wherein the bridge molecule comprises a chemically synthesized bridge molecule.
8. The sensor of any of examples 1-7, wherein the bridge molecule comprises a linear biopolymer.
9. The sensor of any of examples 1-8, wherein the bridge molecule comprises an end-to-end length of less than a persistence length of the bridge molecule.
10. The sensor of any of examples 1-9, wherein the bridge molecule comprises an end-to-end length configured to approximate the sensor gap dimension.
11. The sensor as in any of examples 1-10, wherein the bridge molecule comprises a nucleic acid duplex.
12. The sensor of example 11, wherein the nucleic acid duplex comprises one of a DNA duplex, a DNA-RNA hybrid duplex, a DNA-PNA hybrid duplex, a PNA-PNA duplex, and a DNA-LNA hybrid duplex.
13. The sensor of example 11, wherein the nucleic acid duplex comprises a thiol-modified oligo.
14. The sensor of any of examples 6-13, wherein one of the first self-assembling anchor and the second self-assembling anchor comprises a 5'-thiol modified nucleotide.
15. The sensor of example 11, wherein the nucleic acid duplex further comprises an internal biotin-modified nucleotide.
16. The sensor of any of examples 1-15, wherein the bridge molecule comprises a peptide sequence, and wherein one of the first self-assembling anchor and the second self-assembling anchor comprises an L-cysteine residue.

17. The sensor as in any one of examples 1-16, wherein the bridge molecule is configured to self-assemble to produce a bridge molecule conformation when a fluid medium comprising the bridge molecule is contacted with one of the first contact and the second contact.

18. The sensor of any one of examples 1-17, further comprising a probe, wherein the probe is attached to the bridge molecule.

19. The sensor of any one of examples 1-18, further comprising a linker attached to the bridge molecule.

20. The sensor of any one of examples 18-19, wherein the probe is configured to engage a single target molecule.

21. The sensor of any of examples 1-20, wherein the molecular bridge and/or probe comprises an enzyme.

22. The sensor of example 21, wherein the enzyme is one of a polymerase and a reverse transcriptase.

23. The sensor of any of examples 20-22, wherein the target molecule comprises a plurality of target molecules features, each target molecule feature having a discrete position, including a first target molecule feature at a first position, a second target molecule feature at a second position, and an nth target molecule feature at an nth position.

24. The sensor of example 18, wherein the probe is an enzyme configured to engage the target molecule during a reaction in a solution comprising a plurality of different target molecules, wherein the reaction comprises a time period t, and wherein contacting the target molecule produces a plurality of conformation changes in the enzyme in response to the plurality of target molecule features, wherein each of the plurality of configuration changes modulates an electrical current in the sensor to produce a signal feature.

25. A system comprising a sensor according to any of examples 1-24.

26. The system of claim 25, further comprising a signal processing system coupled to the sensor and configured to detect the signal feature.

27. The system of any of examples 25-26 or the sensor according to any of examples 1-24, wherein the sensor is configured to produce a signal trace comprising a plurality of signal features detected over time period t.

28. The system of any of examples 25-27, further comprising a signal interpretation device.

29. The system of example 28, wherein the signal interpretation device comprises a signal interpretation map.

30. The system of any of examples 28-29, wherein the signal interpretation map is calibrated against a signal trace from a known target sequence.

31. The system of any of examples 28-30, wherein the signal interpretation device is configured to return a signal interpretation in response to the signal trace produced by a target sequence.

32. The system of any of examples 28-31, wherein the signal interpretation includes a probabilistic evaluation of a likelihood that a signal trace interpretation matches a possible actual sequence.

33. A method comprising:
providing a sensor according to any of examples 1-24, 27;
contacting a nucleic acid template with a polymerase, wherein the polymerase is coupled to a bridge molecule comprising a portion of a sensor;
optionally applying an electrical potential to the sensor;
providing a nucleotide base mix;
performing, by the polymerase, an incorporation event comprising incorporation of a nucleotide from the nucleotide base mix into a synthesized nucleic acid; and
detecting a signal produced by the incorporation event.

34. The method of example 33, further comprising a series of incorporation events performed in a time period t, wherein the series of incorporation events produces a signal trace comprising a sequence of signal features.

35. The method of example 34, wherein each signal feature corresponds to one of the series of incorporation events.

36. The method of any of examples 34-35, wherein the signal trace further comprises noise, and wherein the method further comprises removing the noise from the signal trace.

37. The method of any of examples 34-36, wherein each incorporation event produces polymerase kinetic signature that is template base-dependent.

38. The method of any of examples 34-37, wherein the polymerase kinetic signature contributes to the signal feature.

39. The method of any of examples 33-38, wherein the method is suitable to distinguish a first signal feature produced in response to an unmodified template nucleotide and a second signal feature produced in response to a modified template nucleotide.

40. The method of example 39, wherein the modified template nucleotide is one of $N^6$-methyladenosine, $N^4$-methylcytosine, 5-methylcytosine, 5-hydroxymethylcytosine, 5-formylcytosine, and 5-carboxylcytosine.

41. The method of example 39, wherein the modified template nucleotide is an abasic site.

42. A method of manufacturing a biomolecular sensing device comprising:
forming a first electrode and a second electrode on a substrate surface, wherein the first electrode and the second electrode are separated by an electrode gap;
placing a first contact on the first electrode and a second contact on the second electrode, wherein the first contact and the second contact are separated by a contact gap; and
attaching a bridge molecule to the first contact and the second contact.

43. The method of example 42, further comprising contacting the bridge molecule with a probe to couple the probe to the bridge molecule, wherein the probe is coupled to the bridge molecule by self-assembly.

44. The method of any of examples 42-43, wherein attaching the bridge molecule to the first contact and the second contact comprises a self-assembly step.

45. The method of any of examples 42-44, wherein the electrode gap and/or the contact gap is between about 5 nm and about 30 nm.

46. The method of any of examples 42-45, wherein the first contact and/or the second contact comprise gold nanoparticles with a diameter of about 5 nm.

47. The method of any of examples 42-46, wherein a first contact position and/or a second contact position is determined using a lithography method.

48. The method of any of examples 42-47; further comprising placing a photoresist layer over the substrate surface comprising the first electrode and the second electrode, and defining a first contact position and a second contact position using a lithography method.

49. The method of any of examples 42-48, further comprising applying a surface derivatization treatment to the substrate surface at the first contact position and the second contact position.

50. The method of example 49, wherein the surface derivatization treatment comprises silanization.

51. The method of any of examples 42-50, further comprising depositing a gold layer and performing a lift-off step to leave a first gold contact disposed on the first electrode and/or a second gold contact disposed on the second electrode.

52. The method of any of examples 42-51, further comprising contacting the device with a solution comprising a plurality of gold nanoparticles and introducing a first gold nanoparticle at the first contact position and/or a second gold particle at the second contact position.

53. The method of any of examples 42-52, wherein the bridge molecule is attached to the first contact and the second contact by self-assembly prior to contacting the bridge molecule with a/the probe.

54. The method of any of examples 42-53, wherein the bridge molecule is contacted with the probe to produce a sensor complex by self-assembly prior to attaching the bridge molecule to the first contact and the second contact by self-assembly.

55. The method of any of examples 42-54, further comprising fabricating an integrated circuit electronically coupled to the first electrode and the second electrode, 56. The method of example 55, wherein the integrated circuit, the first electrode, and the second electrode comprise a mixed-signal integrated circuit.

57. The method of example 56, wherein the integrated circuit, the first electrode, and the second electrode are fabricated using a CMOS fabrication method.

58. The method of any of examples 42-57, wherein the first and second contact are fabricated using a CMOS fabrication method.

59. The method of any of examples 55-58, wherein the integrated circuit, the first electrode, and the second electrode are fabricated using a fabrication method suitable to produce a field effect transistor.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Although the various examples and embodiments described herein refer to methods of signal detection in relation to nucleic acid targets, the devices and methods of the present disclosure are in no way limited to applications comprising detection and sequencing of nucleic acids. Likewise, although the various examples and embodiments described herein refer to sensors comprising biopolymer bridges molecules, chemically synthesized bridge molecules are within the scope of the present disclosure. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A sensor device comprising:
   a first contact coupled to a first electrode;
   a second contact coupled to a second electrode;
   a sensor gap defined between one of the first contact and the first electrode and one of the second contact and the second electrode;
   a bridge molecule comprising a first end and a second end; wherein the bridge molecule comprises a biopolymer, and wherein the bridge molecule is coupled to the first contact at the first end and coupled to the second contact at the second end; and
   a probe molecule coupled to the biopolymer to form a sensor complex,
   wherein the probe molecule is coupled to the biopolymer by a precisely positioned linker comprising a streptavidin-biotin complex,
   wherein the sensor complex is configured to interact with at least one target molecule.

2. The sensor device of claim 1, wherein the sensor gap has a sensor gap dimension of between about 5 nm and about 30 nm.

3. The sensor device of claim 1, wherein the first end comprises a first self-assembling anchor and the second end comprises a second self-assembling anchor.

4. The sensor device of claim 1, wherein the biopolymer comprises a linear biopolymer.

5. The sensor device of claim 4, wherein the linear biopolymer comprises an end-to-end length that is less than a persistence length of the linear biopolymer.

6. The sensor device of claim 4, wherein the linear biopolymer comprises an end-to-end length configured to approximate a sensor gap dimension of between about 5 nm and about 30 nm.

7. The sensor device of claim 1, wherein the probe molecule comprises an enzyme configured to engage the target molecule.

8. The sensor device of claim 7, wherein the enzyme is a polymerase or a reverse transcriptase.

9. A sensor device comprising:
   a first electrode overlying a substrate surface;
   a second electrode overlying the substrate surface;
   a sensor gap defined between the first electrode and the second electrode;
   a bridge molecule comprising a first end and a second end; wherein the sensor gap comprises a sensor gap dimension of between about 5 nm and about 30 nm; wherein the bridge molecule comprises a biopolymer bridge molecule; and wherein the bridge molecule is coupled to the first contact at the first end and coupled to the second contact at the second end; and
   a probe molecule attached to the biopolymer bridge molecule,
   wherein the probe molecule is attached to the biopolymer bridge molecule by a precisely positioned linker comprising a streptavidin-biotin complex,
   wherein the probe molecule is configured to engage at least one target molecule.

10. The sensor device of claim 9, wherein the first end comprises a first self-assembling anchor and the second end comprises a second self-assembling anchor.

11. The sensor device of claim 10, wherein one of the first self-assembling anchor and the second self-assembling anchor comprises a 5'-thiol modification.

12. The sensor device of claim 10, wherein the biopolymer bridge comprises a peptide sequence, and wherein one of the first self-assembling anchor and the second self-assembling anchor comprises a cysteine residue or a peptide configured to selectively bind gold, aluminum, silicon dioxide, palladium, platinum, or other metals or material contacts capable of thiol-metal binding.

13. The sensor device of claim 9, wherein the biopolymer bridge molecule comprises a linear biopolymer.

14. The sensor device of claim 13, wherein the linear biopolymer comprises an end-to-end length that is less than a persistence length of the linear biopolymer.

15. The sensor device of claim 14, wherein the linear biopolymer comprises an end-to-end length configured to approximate the sensor gap.

16. The sensor device of claim 9, wherein the probe molecule comprises an enzyme configured to engage the target molecule.

17. The sensor device of claim 16, wherein the enzyme is a polymerase or a reverse transcriptase.

18. The sensor device of claim 16, wherein the enzyme is configured to engage the target molecule during a reaction in a solution comprising a plurality of different target molecules, wherein the reaction comprises a time period t, and wherein contacting the target molecule produces a plurality of conformational changes in the enzyme in response to the plurality of target molecule features, wherein each of the plurality of conformational changes modulates an electrical measurement in the sensor to produce a signal feature.

19. The sensor device of claim 18, further comprising a signal processing system configured to detect the signal feature.

20. The sensor device of claim 18, wherein the sensor device is configured to produce a signal trace comprising a plurality of signal features detected over time period t.

21. The sensor device of claim 9, wherein the biopolymer bridge molecule comprises a nucleic acid duplex.

22. The sensor device of claim 21, wherein the nucleic acid duplex comprises a DNA duplex, a DNA-RNA hybrid duplex, a DNA-PNA hybrid duplex, a PNA-PNA duplex, or a DNA-LNA hybrid duplex.

23. The sensor device of claim 21, wherein the nucleic acid duplex comprises a thiol-modified oligonucleotide.

24. The sensor device of claim 21, wherein the nucleic acid duplex further comprises an internal modification.

25. The sensor device of claim 9, further comprising a signal interpretation device, wherein the signal interpretation device comprises a signal interpretation map, and wherein the signal interpretation map is calibrated against a signal trace from a known target sequence.

* * * * *